United States Patent
Nesterenko et al.

(10) Patent No.: US 11,783,937 B2
(45) Date of Patent: Oct. 10, 2023

(54) ADAPTIVE CONTROL OF MEDICAL DEVICES BASED ON CLINICIAN INTERACTIONS

(71) Applicant: CareFusion 303, Inc., San Diego, CA (US)

(72) Inventors: Igor Nesterenko, San Diego, CA (US); Lisa Diggett, Olathe, KS (US); Evan Chen, San Diego, CA (US); Greg T. Hulan, Poway, CA (US); Jeff Gaetano, Wittmann, AZ (US); Karthi Rajendran, San Diego, CA (US); Robert Regedanz, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 464 days.

(21) Appl. No.: 16/911,151

(22) Filed: Jun. 24, 2020

(65) Prior Publication Data

US 2020/0402651 A1 Dec. 24, 2020

Related U.S. Application Data

(60) Provisional application No. 62/897,199, filed on Sep. 6, 2019, provisional application No. 62/865,906, filed on Jun. 24, 2019.

(51) Int. Cl.
  *G16H 40/60* (2018.01)
  *G16H 40/20* (2018.01)
  (Continued)

(52) U.S. Cl.
  CPC ....... *G16H 40/20* (2018.01); *G06Q 10/06398* (2013.01); *G06Q 10/063116* (2013.01);
  (Continued)

(58) Field of Classification Search
  None
  See application file for complete search history.

(56) References Cited

U.S. PATENT DOCUMENTS

| | | | |
|---|---|---|---|
| 9,142,117 B2 * | 9/2015 | Muhsin | G06F 16/24568 |
| 2008/0282204 A1 | 11/2008 | Del Valle Lopez | |
| 2009/0043634 A1 | 2/2009 | Tisdale | |
| 2010/0191583 A1 * | 7/2010 | Mackenzie | G06Q 10/063112 |
| | | | 705/7.14 |
| 2013/0162424 A1 * | 6/2013 | Treacy | G16H 40/20 |
| | | | 340/502 |

(Continued)

FOREIGN PATENT DOCUMENTS

WO  WO-2017088026  6/2017

OTHER PUBLICATIONS

International Search Report and Written Opinion for Application No. PCT/US2020/039455, dated Aug. 28, 2020, 17 pages.

*Primary Examiner* — John A Pauls
(74) *Attorney, Agent, or Firm* — Morgan, Lewis & Bockius LLP

(57) ABSTRACT

A method and system identifies interactions of a user with one or more medical devices, determines, based on the one or more interactions and a predetermined set of rules, a compliance score associated with the first user, in response to the compliance score not satisfying a threshold compliance score, and reducing an access level of the user to at least one of the one or more medical devices and generates a training program associated with the at least one medical device and the one or more interactions, and automatically, without user involvement, sends a training package associated with the training program to the user and notifies the user to complete the training program using the training package. The system and method also generates a new shift schedule for clinicians responsive to a first shift schedule not (Continued)

satisfying criteria and the clinicians not satisfying respective performance scores.

22 Claims, 13 Drawing Sheets

(51) Int. Cl.
*G16H 20/17* (2018.01)
*G16H 10/60* (2018.01)
*G16H 50/20* (2018.01)
*G16H 70/20* (2018.01)
*G06Q 10/0631* (2023.01)
*G06Q 10/0639* (2023.01)
*G06Q 30/018* (2023.01)
*G09B 19/00* (2006.01)
*H04L 9/40* (2022.01)
*G06F 3/14* (2006.01)

(52) U.S. Cl.
CPC ......... *G06Q 30/018* (2013.01); *G09B 19/003* (2013.01); *G16H 10/60* (2018.01); *G16H 20/17* (2018.01); *G16H 40/60* (2018.01); *G16H 50/20* (2018.01); *G16H 70/20* (2018.01); *H04L 63/08* (2013.01); *G06F 3/14* (2013.01)

(56) References Cited

U.S. PATENT DOCUMENTS

| | | | | |
|---|---|---|---|---|
| 2013/0332194 A1* | 12/2013 | D'Auria | ................ | G16H 10/60 705/3 |
| 2014/0032231 A1* | 1/2014 | Semen | ................... | G16H 40/63 705/2 |
| 2014/0195295 A1* | 7/2014 | Whitley | ............. | G06Q 10/0633 705/7.27 |
| 2014/0322682 A1 | 10/2014 | Baym et al. | | |
| 2015/0066531 A1* | 3/2015 | Jacobson | ............... | G16H 20/17 705/2 |
| 2015/0227710 A1* | 8/2015 | Pappada | ................ | G16H 70/20 705/2 |
| 2015/0332006 A1* | 11/2015 | Swanson | ................ | G16H 40/67 705/2 |
| 2016/0191519 A1* | 6/2016 | Surendrakumar | .... | H04L 63/105 726/7 |
| 2016/0358493 A1 | 12/2016 | Bilic et al. | | |
| 2017/0068792 A1* | 3/2017 | Reiner | ............... | A61B 17/1214 |
| 2017/0109480 A1* | 4/2017 | Vahlberg | ................ | G16H 40/20 |

* cited by examiner

ADAPTIVE CONTROL OF MEDICAL DEVICES BASED ON CLINICIAN INTERACTIONS

CROSS-REFERENCE TO RELATED APPLICATIONS

This application claims the benefit of priority as a nonprovisional of U.S. Application Ser. No. 62/897,199, entitled "ADAPTIVE CONTROL OF MEDICAL DEVICES BASED ON CLINICIAN INTERACTIONS," filed on Sep. 6, 2019, and claims the benefit of priority as a nonprovisional of U.S. Application Ser. No. 62/865,906, entitled "SYSTEMS AND METHODS FOR IDENTIFYING NON-COMPLIANCE PATTERNS OF INTERACTIONS WITH A MEDICAL DEVICE," filed on Jun. 24, 2019, the entirety of each of which is incorporated herein by reference.

TECHNICAL FIELD

This application relates generally to controlling medical devices based on an evaluation of clinicians and their respective interactions with medical devices in a healthcare organizations.

BACKGROUND

Medical devices, such as infusion devices, provide various conveniences and simplify administration of medications to patients by clinicians, such as nurses, of a health care facility. Healthcare facilities and the medical device manufacturers may establish various protocols and/or safeguards to ensure that the fluid or medication is administered safely and consistently by different clinicians with different experiences and levels of training. However, due to the different experiences and levels of training, actions of some clinicians may fall outside of a healthcare facility's protocols, and risk safety of the patient and operations of the healthcare facility. Moreover, healthcare organizations utilize various systems from various vendors and clinicians with varying levels of proficiency with the systems to assist in the treatment of the patients. Accordingly, one concern healthcare organizations is to identify and reduce operational risks to the healthcare organization while improving operational efficiency. Existing healthcare systems, however, do not adequately identify the clinicians with low levels of proficiency with one or more of the utilized systems, thus increasing risk of injury to the patient and/or decreasing operational efficiency of the healthcare organization.

SUMMARY

Various interactions of clinicians with different medical devices and systems may increase operational risks for a healthcare organization. For example, a clinician may fail to follow one or more protocols in administering medications to patients. Existing systems are not suitably configured to track and monitor non-compliant clinician interactions across multiple medical devices. Healthcare organizations may also face operational risks from temporary or traveling clinicians with varying levels of training and expertise at using the different medical devices and systems of the healthcare organization. Existing systems also cannot automatically provide such clinicians with assistance to successfully complete their tasks in a manner to satisfy the best practices and/or protocols standards or efficiently identify source centers with well-trained temporary clinicians to reduce the operational risks. Furthermore, existing systems and methods do not allow for healthcare organizations for efficiently specifying scheduling criteria and scheduling clinicians for shifts at a healthcare organization based on the scheduling criteria. Additionally, operational risks of a healthcare organization may increase due to improper and/or inefficient scheduling of clinicians for different shifts at the healthcare organization.

Accordingly, there is a need for systems and methods that can track individual clinician interactions, identify non-compliant interactions, generate training plans to address and/or rectify the non-compliant interactions, thereby reducing the risk to patients and/or a healthcare facility from non-compliant clinicians. There is also a need for systems and methods that can identify clinicians that do not adhere to the best practices and/or protocols of a healthcare organization, adapt the operation of a device within the organization to provide them with assistance to satisfy the best practices and/or protocols standards, identify source centers for additional well-trained clinicians, and allow scheduling systems of healthcare organizations to dynamically and efficiently schedule clinicians based on schedule criteria specified to reduce operational risks. The systems and methods disclosed herein are able to effectively identify non-compliant interactions of a clinician and address them via training plans generated for that clinician, thereby reducing operational risks by increasing safety of the medical devices and systems used while treating patients.

According to various implementations, a method includes identifying one or more interactions of a first user with one or more medical devices; determining, based on the one or more interactions and a predetermined set of rules, a compliance score associated with the first user; in response to the compliance score not satisfying a threshold compliance score, reducing an access level of the first user to at least one of the one or more medical devices and generating a training program associated with the at least one medical device and the one or more interactions, wherein reducing the access level includes reducing a number of respective features of the at least one medical device that are available to the first user; and automatically, without user involvement, sending a training package associated with the training program to the first user and notifying the first user to complete the training program using the training package.

According to some implementations, a method includes tracking one or more interactions of a first user with one or more medical devices; determining, based on a set of stored rules and the one or more interactions, a compliance score; determining whether the compliance score satisfies a threshold compliance score; in response to determining that the compliance score satisfies the threshold compliance score, generating, based on the one or more interactions, a training plan for the first user; and adjusting, based on the training plan, one or more features of the one or more medical devices available for the first user at the one or more medical devices.

In accordance with some implementations, a method includes identifying interactions of a plurality of clinicians with one or more medical devices, and generating, based on a set of stored rules and one or more interactions of each user of the plurality of clinicians, a performance score for each of plurality of clinicians associated with the interactions. The method includes receiving a first shift schedule associated with the plurality of clinicians, and determining whether the first shift schedule satisfies one or more scheduling criteria associated with the healthcare facility. In response to determining that the first shift schedule does not satisfy the one or more scheduling criteria and a first performance score for a first clinician does not satisfying a first evaluation threshold of the one or more scheduling criteria, (1) generating a training plan for the clinician, or a new second shift schedule for the plurality of clinicians that replaces a first clinician scheduled during a first time period with a second clinician not currently scheduled during the time period based on a second performance score of the second clinician, and (2) electronically preventing the first clinician from using at least one of the plurality of medical devices during the first time period. The method includes causing the new schedule for the shift, or the training plan, to be displayed on a display device associated with a clinician scheduling system.

Other aspects include corresponding systems, apparatus, and computer program products for implementation of the foregoing methods.

In accordance with some implementations, a system includes a memory storing instructions and one or more processors coupled with the memory and configured to execute the instructions to cause the system to identify interactions of a plurality of clinicians with one or more medical devices, generate, based on a set of stored rules and one or more interactions of each user of the plurality of clinicians, a performance score for each of plurality of clinicians, receive a first shift schedule associated with the plurality of clinicians. The one or more processors are configured to execute the instructions to cause the system to determine whether the first shift schedule satisfies one or more scheduling criteria associated with the healthcare facility, and when the first shift schedule does not satisfy the one or more scheduling criteria and a first performance score for a first clinician not satisfying a first evaluation threshold of the one or more scheduling criteria, (1) generate a new second shift schedule for the plurality of clinicians that replaces a first clinician scheduled during a first time period with a second clinician not currently scheduled during the time period based on a second performance score of the second clinician, and (2) electronically prevent the first clinician from using at least one of the plurality of medical devices during the first time period. The one or more processors configured to execute instructions to cause the system to cause the new schedule for the shift to be displayed on a display device associated with a clinician scheduling system. Other aspects include corresponding systems, apparatus, and computer program products for implementation of the system.

In accordance with some implementations, a device management server includes one or more processors and memory storing one or more programs configured for execution by the one or more processors. The one or more programs include instructions for performing the operations of any of the methods described in this application. In accordance with some implementations, a non-transitory computer-readable storage medium stores instructions that, when executed by a server system, cause the server system to perform the operations of any of the methods described in this application.

BRIEF DESCRIPTION OF THE DRAWINGS

For a better understanding of the various described implementations, reference should be made to the Detailed Description below, in conjunction with the following drawings. Like reference numerals refer to corresponding parts throughout the figures and description.

Figure 1A:
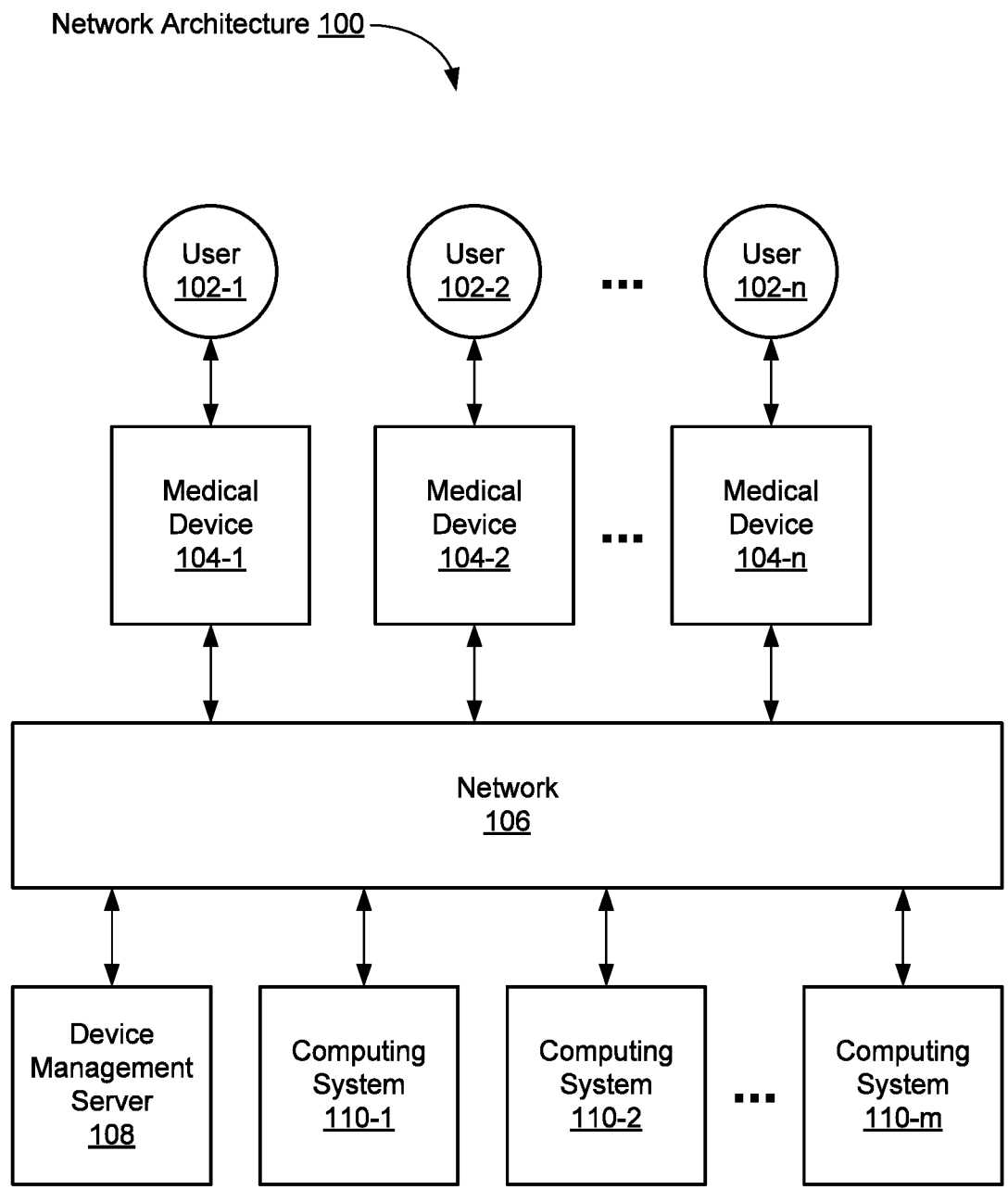
FIG. 1A is a block diagram of an example network architecture for determining non-compliance patterns of clinicians according to illustrative implementations.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various configurations of the subject disclosure and is not intended to represent the only configurations in which the subject disclosure may be practiced. The appended drawings are incorporated herein and constitute a part of the detailed description. The detailed description includes specific details for the purpose of providing a thorough understanding of the subject disclosure. However, it will be apparent to those skilled in the art that the subject disclosure may be practiced without these specific details. In some instances, structures and components are shown in block diagram form in order to avoid obscuring the concepts of the subject disclosure. Like components are labeled with identical element numbers for ease of understanding.

The terminology used in the description of the various implementations described herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will also be understood that, although the terms "first" and "second" are used herein to describe various elements, these elements should not be limited by these terms. These terms are used only to distinguish one element from another. It will be further understood that the terms "includes," "including," "comprises," and/or "comprising" when used in the specification, specify the presence of stated features, steps, operations, elements, and/or components, but do not preclude the presence or addition of one or more other features, steps, operations, elements, components, and/or groups thereof. A clinician may include a licensed or unlicensed individual responsible for operating, maintaining, servicing, delivering, or otherwise interacting with a medical device in, by, or for a healthcare organization. As used herein, examples of a healthcare organization include hospitals, long-term care facilities, nursing homes, out-patient treatment centers, store-front retail treatment centers, pharmacies, community clinics, non-acute care facilities, acute care facilities, and the like.

According to various aspects, the subject technology provides a means to identify users, either by individual or role, so that clinical actions and other actions may be associated with the users. In this regard, medical devices may be configured with a radio-frequency identification (RFID) tag readers to wirelessly receive data related to a clinician's identifying information stored in an RFID tag, such as a clinician's badge or identification card. The medical devices may be configured to grant or deny access to one or more protected functions of the medical devices and/or computing systems associated with a health care facility based on the received clinician's identifying information, a set of passcodes associated with one or more permissions, and/or one or more badges of clinicians associated with one or more permissions. Protected functions may include, but are not limited to, unlocking a medical device, special clinical functions or workflows of the medical devices (e.g., infusion of restricted and/or classified drugs), access to biomed service features (e.g., cleaning mode and/or features of medical devices, maintenance mode and/or features of medical devices, and the like), and other similar functions of a medical device.

According to various implementations, the disclosed medical devices may identify new users associated with a health care facility without requiring pre-registration at a central computing system, node, and/or server. For example, in response to a clinician attempting to access a protected function of a medical device, such as unlocking the medical device, attempting to access a restricted function, and the like, the medical device may display a prompt on a display device associated with the medical device to provide clinician identifying information, such as by scanning their badge. The medical device may be configured to determine whether the received clinician identifying information exists in one or more data storage units associated with the medical device. If the medical device determines that the clinician's identifying information does not exist, then the medical device may display a prompt on the display device associated with the medical device to enter a passcode of the clinician. In response to determining that the entered passcode is valid, the medical device may identify permissions associated with the passcode and based on the associated permissions, the medical device may grant and/or deny access to the function to the clinician. In some implementations, the use of passcodes allows a clinician to access one or more functions of a medical device without scanning a badge and/or if the clinician is without a badge.

The medical device may transmit a message to the device management server identifying the badge information received from the clinician and the associated permissions. The device management server may be configured to automatically store the badge information in association with the permissions in one or more data storage units associated with the device management server and/or update a master list of clinician badges and associated permissions. The device management server may automatically transmit new badge information and associated permissions to other medical devices of the healthcare facility.

The subject technology may also include a device management server configured to identify and track interactions of clinicians (e.g., nurses) with medical devices in a healthcare organization (e.g., hospital) and, based on the clinicians' interactions with the medical devices, the device management server may determine a number of times when a medication is administered outside of a predetermined medication administration parameter value (e.g., dosage). If the number satisfies a threshold, the device management server may add the medication to a set of medications that are administered outside of predetermined drug administration parameter values. In some implementations, the device management server may be configured to provide one or more alerts to a user (e.g., pharmacist, pharmacy technician, and the like) indicating the set of medications that are administered outside of predetermined drug administration parameter values. In this regard, in some implementations, the device management server may provide and/or indicate corresponding entries of the set of medications in a drug library of a drug management system of the healthcare organization. In some implementations, the device management server may be configured to determine changes to the respective entries of the set of medications based on data related to administration of a medication by the clinicians (e.g., a dosage at which a medication is administered).

In some implementations, the device management server may generate a score for one or more clinicians based on interactions of clinician with the medical device, and schedule the clinicians into different shifts based on the scores of the clinicians. In some implementations, the device management server may be configured to schedule shifts of clinicians to include a predetermined percentage or ratio of clinicians with high scores and clinicians with lower scores. In some implementations, for one or more low scoring clinicians that are scheduled in a shift, the device management server may schedule clinicians assigned as mentors to the low scoring clinicians in that same shift. In some implementations, a healthcare organization may temporarily staff one or more clinicians from various clinician staffing agencies, and, based on the clinicians' scores, the device management server may be configured to request clinicians from the clinician staffing agency associated with a majority of the clinicians with high scores. In some implementations, the device management server may generate and/or update a score for a clinician based on the interactions of the clinician with different medical devices.

In some implementations, for clinicians with low scores, the device management server may be configured to provide one or more reminders or follow-up steps that the clinician should perform next. Examples of such steps may include, but are not limited to, checking for device settings, checking vital signs, and the like. In some implementations, the device management server may display one or more steps related to a procedure (e.g., medication administration procedure) on a display device associated with the medical device while the clinician is performing the procedure using the medical device. Additional details of the subject technology are described herein with reference to FIGS. 1-12.

FIG. 1A is a block diagram of a network architecture 100 in accordance with some implementations of the subject technology.

The network architecture 100 includes one or more medical devices 104-1, 104-2, . . . , 104-n, collectively referred to herein as medical devices 104. The one or more medical devices 104 may be communicatively coupled to a device management server 108 and/or one or more computing systems of the healthcare facility 110-1, 110-2, . . . , 110-m, collectively referred to herein as computing systems 110, by one or more communication networks 106. Examples of the one or more communication networks include, but are not limited to, an intranet, the Internet, cellular telephone networks, mobile data networks, wide area networks, local area networks, metropolitan area networks, and the like. In some implementations, the one or more communication networks 106 include a public communication network (e.g., the Internet and/or a cellular data network), a private communications network (e.g., a private LAN or leased lines), or a combination of such communication networks. The device management server 108 may be configured to communicate with the medical devices 104 and/or the computing systems 110.

The device management server 108 may be configured to receive and/or transfer clinician related data from and/or to the medical devices 104 and/or the computing systems 110. Examples of clinician related data include, but are not limited to, clinician identifiers, clinician biographical information, information related to clinician training plans, and the like.

In some implementations, the device management server 108 may be a single computing device such as a computer server, while in other implementations, the device management server 108 is implemented by multiple computing devices working together to perform the actions of a server system (e.g., cloud computing). Additional details of the device management server 108 are described herein and with reference to FIG. 2.

The medical devices 104 may include one or more input devices (shown in FIG. 3) configured to receive inputs to the medical devices 104. The clinicians, such as users 102-1, 102-2, . . . , 102-n, collectively referred to herein as users 102, may interact with the one or more medical devices 104 via the one or more input devices. The users 102 may utilize the medical devices 104 to access the device management server 108 and/or computing systems 110 to participate in corresponding services provided by the device management server 108 and/or computing systems 110.

Figure 1B:
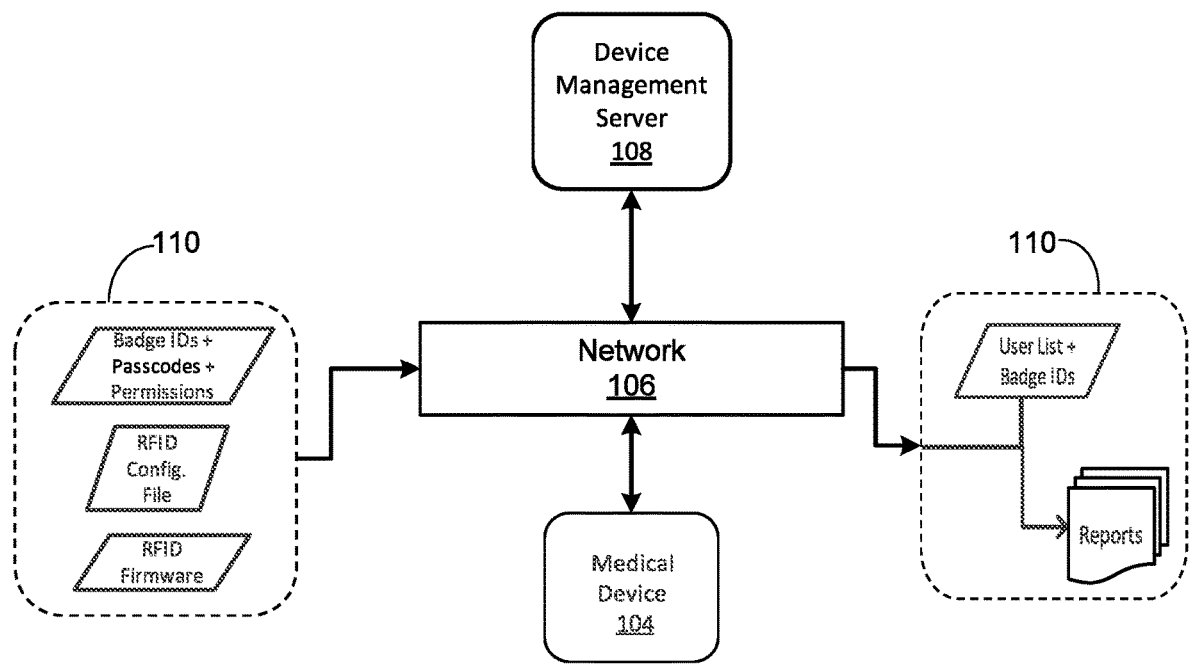
FIG. 1B is a block diagram of an example device management server in communication with a medical device, and computing systems of a healthcare facility, according to illustrative implementations.
Figure 4:
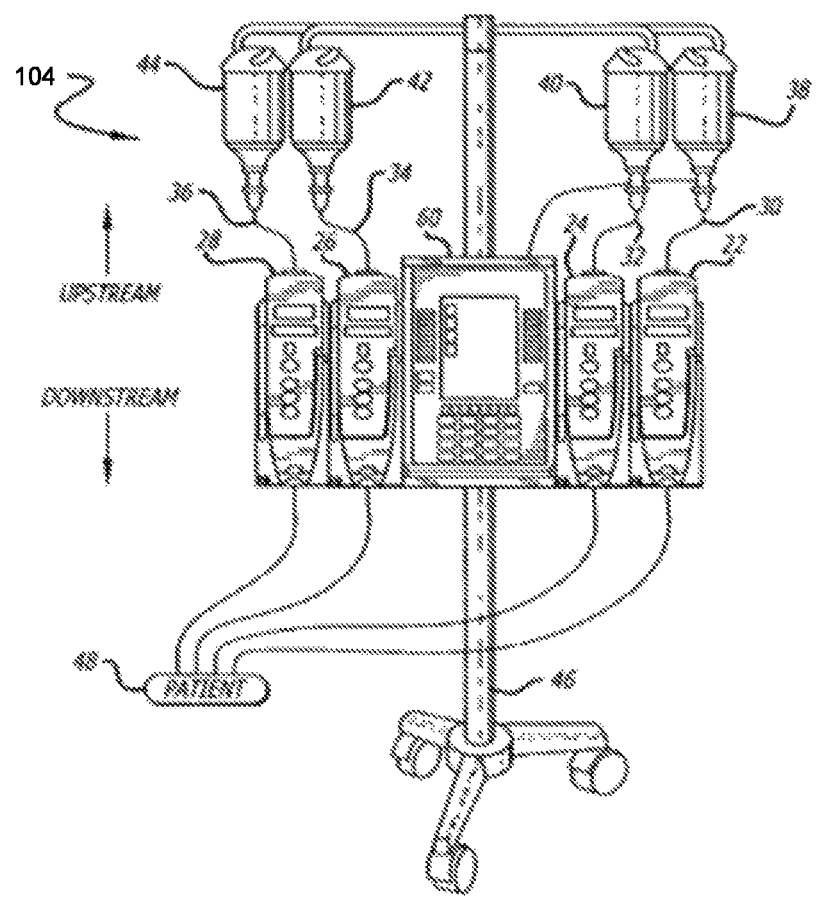
FIG. 4 is an example medical device which may be interacted with by a clinician within in a healthcare organization

Turning now to FIG. 1B, there is shown a block diagram of a device management server 108 in communication with a medical device 104, and computing systems 110. As described previously, device management server 108 may communicate with medical device 104 over network architecture 100. In some implementations, as depicted in FIG. 4, the medical device 104 may include a programming module 60 configured to be connected to one or more functional modules.

The device management server 108 may be configured to receive, from a computing system 110, data related to one or more badges and/or passcodes of clinicians, and the permissions for one or more functions of one or more medical devices 104 associated with the badges and/or passcodes, as shown in FIG. 1B. In some implementations, data related to a badge and/or passcode of a clinician and the associated permissions may be collected via a computing system 110 of the healthcare facility during an onboarding process of adding the clinician to one or more administration systems (e.g., employee database, and the like) of the healthcare facility. The device management server 108 may be configured to receive configuration data and/or firmware for one or more medical devices 104 communicatively coupled with the device management server 108, as shown in FIG. 1B. The configuration data and/or firmware may be received from one or more other computing systems 110 of the healthcare facility.

The device management server 108 may be configured to transmit the configuration data and/or firmware, the data related to the one or more badges and/or passcodes and the associated permissions to the one or more medical devices 104 communicatively coupled with the device management server 108, as shown in FIG. 1B. The data related to the one or more badges may be associated with clinician identifying information of the one or more clinicians. In some implementations, clinician identifying information may be a unique identifier associated with and/or configured to identify a clinician, such as an employee identifier, a badge identifier, an identifier associated with the clinician in another administration system (e.g., an EMR system) of a health facility, and the like.

The one or more medical devices 104 may be configured to determine whether clinician identifying information provided to the medical devices (e.g., by a clinician scanning a badge using the RFID reader of the medical device), and/or passcodes received from a user of the medical device are valid based on the received data related to the one or more badges and/or passcodes. The medical devices 104 may be configured to grant or deny access to one or more functions (e.g., unlocking a medical device, accessing a restricted function of a medical device, and the like) of the medical devices based on the received data related to the permissions associated with the one or more badges and/or passcodes. For any clinician identifying information that is not found in the received data, the medical devices 104 may be configured to register the associated clinician and transmit the new clinician identifying information to the device management server 108. The device management server 108 may transmit the clinician identifying information along with its associated permissions to other medical devices 104 of the healthcare facility. Additional details of determining whether a clinician's identifying information is valid and granting access to one or more functions of a medical device, and registering a clinician via a medical device 104 are described herein with reference to FIG. 6.

A medical device 104 may be configured to associate a clinician's interactions with the medical device with the received clinician's identifying information (e.g., received badge information) and transmit the data related to the interactions to the device management server 108, as shown in FIG. 1B. The device management sever 108 may be configured to determine a performance score for the clinicians based on the interactions data received from the medical devices 104, and the device management server 108 may be configured to transmit the data related to the performance scores and corresponding clinician identifying information (e.g., badge information of a clinician, passcodes of clinicians, user identifiers of clinicians) to a computing system 110 of the healthcare facility to allow the computing system 110 and/or a user of the computing system 110 to generate reports, such as reports related to clinician performance at the health care facility, as shown in FIG. 1B. The device management server 108 may be configured to disable and/or lock one or more functions of a medical device based on the determined performance scores. Additional details of generating performance scores for clinicians and disabling and/or locking one or more functions of a medical device are described herein with reference to FIGS. 7-11.

Figure 2:
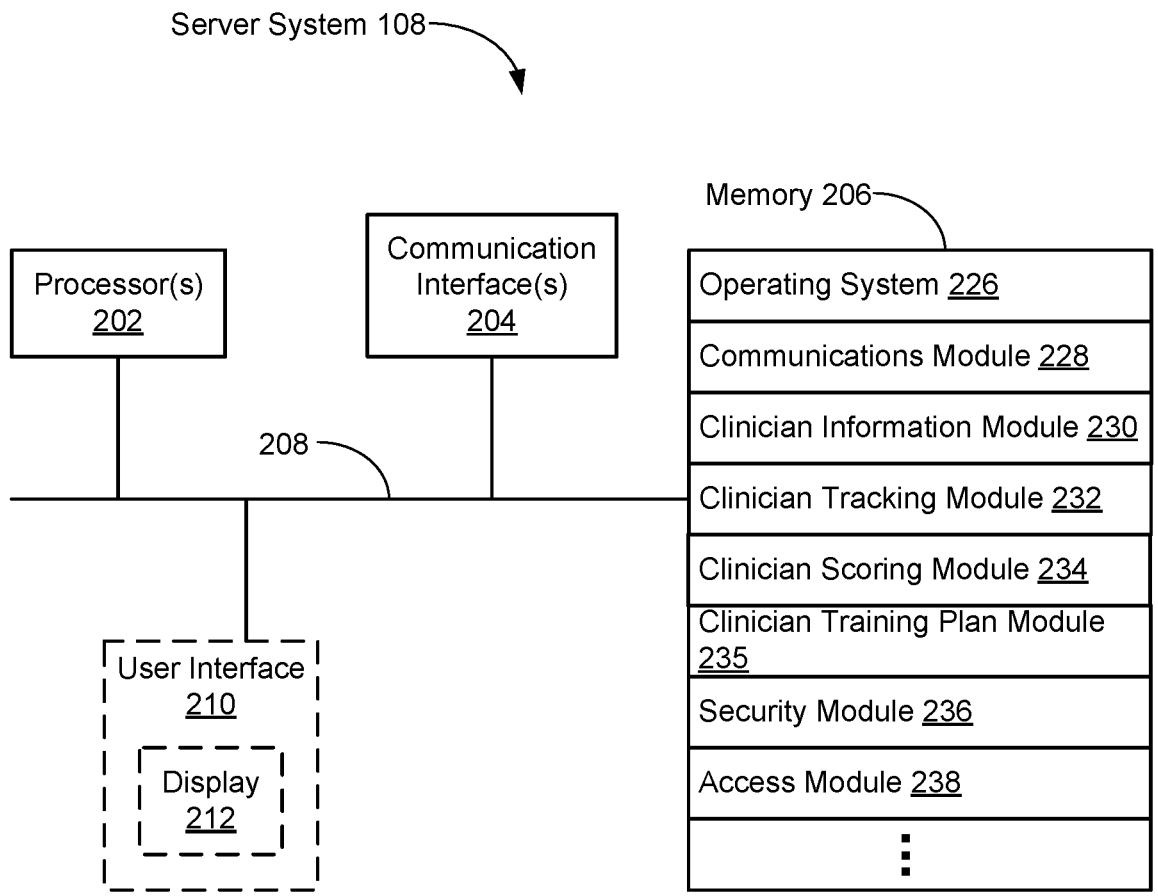
FIG. 2 is a block diagram of an example server system from the architecture of FIG. 1 according to illustrative implementations.

Turning now to FIG. 2, there is shown a block diagram depicting a device management server 108 in accordance with some implementations. The device management server 108 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. In some implementations, the device management server 108 may include a display device 212. In some implementations, the device management server 108 may include input devices such as a keyboard, a mouse, a trackpad, and/or input buttons. In some implementations, the display device 212 may include a touch-sensitive surface, in which case the display is a touch-sensitive display.

The memory 206 may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 206 includes one or more storage devices remotely located from the processor(s) 202. The memory 206, or alternatively the non-volatile memory device(s) within the memory 206, includes a non-transitory computer-readable storage medium. In some implementations, the memory 206 or the computer-readable storage medium of the memory 206 stores programs, modules, and/or data structures that may be used for the performing one or more operations of the device management server 108. For example, the memory 206 may include programs, modules, and/or data structures for an operating system 226, a network communication module 228, a clinician information module 230, a clinician tracking module 232, a clinician scoring module 234, a clinician training plan module 235, a security module 236, and an access device module 238.

In some implementations, the operating system 226 module may include procedures for handling various basic system services and for performing hardware dependent tasks. The network communication module 228 may be configured for connecting the device management server 108 to other computing devices via the one or more communication network interfaces 204 (wired or wireless) and one or more communication networks 106. The clinician information module 230 may be configured to store data related to clinicians including, but not limited to, clinician identifiers, clinician biographical information, current compliance scores of the clinicians, and the like. The clinician tracking module 232 may be configured to track information related to interactions of clinicians with the medical devices 104. The clinician tracking module 232 may be configured track interactions of clinicians over a career of a clinician. The clinician tracking module 232 may be configured to group and/or categorize the interactions of the clinician into one or more groups and/or categories. Additional details of the grouping and/or categorizing the interactions are described herein with reference to FIG. 6.

The clinician scoring module 234 may be configured to generate a score for a clinician based on determining whether one or more interactions are compliant. In some implementations, if the one or more interactions are compliant, then the clinician scoring module 234 may increase the score, and if the one or more interactions are non-compliant, then the clinician scoring module 234 may decrease the score. In some implementations, the clinician scoring module 234 may be configured to generate and/or maintain a score for each group and/or category of interactions. The access module 238 may be configured to grant, deny, and/or modify access to the device management server 108 and/or one or other computing systems or devices communicatively coupled to the device management server 108.

The clinician training plan module 235 may be configured to determine whether one or more interactions are compliant and generate and/or update a compliance score based on whether the one or more interactions are compliant. In some implementations, if the one or more interactions are compliant, then the clinician training plan module 235 may increase the compliance score, and if the one or more interactions are non-compliant, then the clinician training plan module 235 may decrease the compliance score. The clinician training plan module 235 may be configured to generate a training plan based on the compliance score. In some implementations, the clinician training plan module 235 may be configured to generate and/or maintain a compliance score for each group and/or category of interactions, and may generate a training plan for the group and/or category of interactions with a compliance score that satisfies a threshold training plan compliance score. The access module 238 may be configured to grant, deny, and/or modify access to the server system 108 and/or one or other computing systems or devices communicatively coupled to the server system 108.

Figure 3:
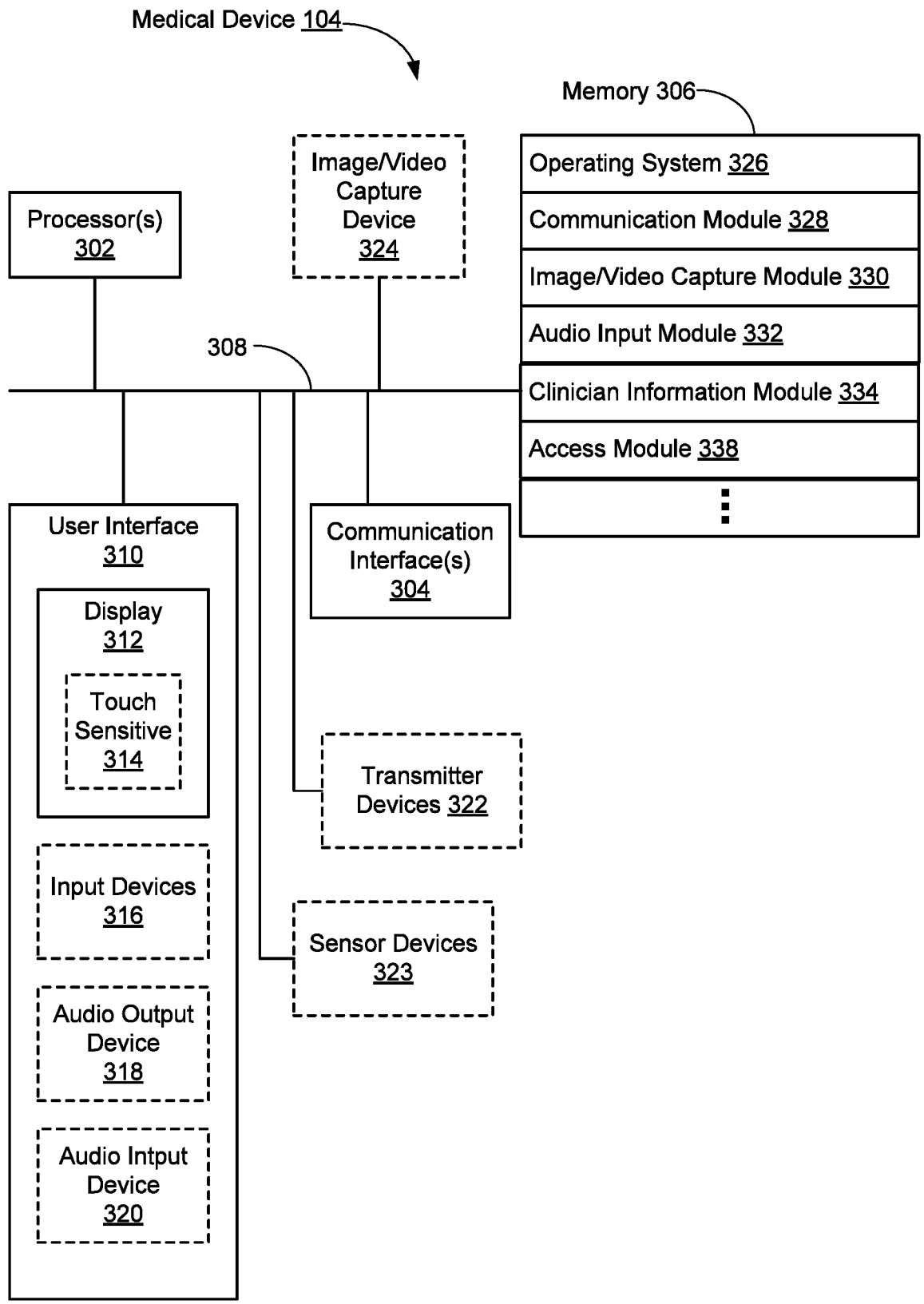
FIG. 3 is a block diagram of an exemplary client device from the architecture of FIG. 1 according to illustrative implementations.

Turning now to FIG. 3, there is shown a block diagram depicting a medical device 104. A medical device 104 may include one or more processors 302, one or more network or communications interfaces 304, memory 306, one or more communication buses 308, a user interface unit 310, transmitter devices 322, and sensor devices 323. The one or more processors 302, the one or more network or communication interfaces 304, memory 306, and the user interface unit 310 may be configured to communicate with one another via the one or more communication buses 308. In some implementations, the communication buses 308 may include circuitry (sometimes called a chipset) that interconnects and controls communications between components of the medical device 104. In some implementations, the medical device 104 may include an image/video capture device 324, such as a camera.

The user interface unit 310 may include a display 312, one or more input devices 316, such as a keyboard or a mouse, one or more audio output devices 318, and/or one or more audio input devices 320. In some implementations, the display 312 may include a touch sensitive display or surface 314, which is configured to receive inputs from a user 102. The one or more audio output devices 318 may include, but are not limited to, speakers, interfaces configured to transfer audio related data to a device configured to project audio, and the like. The one or more input devices 320 may include, but are not limited to, microphones, interfaces configured to receive audio related data from a device configured to receive audio.

The memory 306 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. In some implementations, the memory 306 includes one or more storage devices remotely located from the processor(s) 302. The memory 306, or alternatively the non-volatile memory device(s) within the memory 306, includes a non-transitory computer-readable storage medium. In some implementations, the memory 306 or the computer-readable storage medium of the memory 306 stores the programs, modules, and data structures that may be used for performing operations of the medical device 104 and for performing techniques described herein for identifying non-compliance patterns of interactions with the medical devices 104. The memory 306 may include an operating system 326, a network communication module 328, an image/video capture module 330, an audio input/output module 332, a clinician information module 334, and the like.

The operating system 326 may be configured to perform procedures of execution of various system services of the medical device 104, including, but not limited to, hardware, and software dependent tasks. The network communication module 328 may be configured to execute instructions to connect the medical device 104 to one or more other computing devices, such as the device management server 108, computing systems 110, and the like, via the one or more communication interfaces 304 and communication networks, such as the communication network 106. The image/video capture module 330 may be configured to execute instructions to capture images or a continuous stream of images. The audio input module 332 may be configured process received input data and transmit instructions and/or related data to one or more other components of the medical device 104. The access module 338 may be configured grant, deny, and/or modify access to the medical device 104. For example, the access module 338 may be configured to grant or deny access to the medical device 104 based on received login credentials for the medical device 104.

The above identified modules and applications may correspond to a set of executable instructions for performing one or more functions as described above and/or in the methods described in this application (e.g., the computer-implemented methods and other information processing methods described herein). One or more of the modules may be implemented as a specific hardware device with the appropriate input and output signal paths. The modules may be combined or otherwise re-arranged in various implementations. In some implementations, the memory 206 and/or the memory 306 store a subset of the modules and data structures identified above. In some implementations, the memory 206 and/or the memory 306 stores additional modules and data structures not described above. In some implementations, processors 302 may be configured to execute the above identified modules for performing the one or more above-described functions and/or techniques FIG. 4 is an example medical device which may be interacted with by a clinician within in a healthcare organization. The medical device 104 shown in FIG. 4 may include a programming module 60 configured to be connected to one or more functional modules, such as the four fluid infusion pumps 22, 24, 26, and 28 each of which is in operative engagement with a respective fluid administration set 30, 32, 34, and 36. Fluid supplies 38, 40, 42, and 44, which may take various forms but in this case are shown as bottles, are inverted and suspended above the pumps. Fluid supplies may also take the form of bags or other types of containers. Both the medical device 104 and the fluid supplies 38, 40, 42, and 44 are mounted to a roller stand or pole 46. The specific fluid supplies as well as their orientation (e.g., mount location, mount height, mounting type, etc.) within the care area may be generate one or more interaction records. The interaction record for a set for example may be generated in part by detecting a scannable code associated with the set prior to use. Once scanned, the interaction record may be recorded for use as described herein.

As shown in the example implementation of FIG. 4, each administration set 30, 32, 34, and 36 is connected between a respective fluid supply 38, 40, 42, and 44 and the same patient 48 so that the patient may receive the fluids in all the fluid supplies. The administration set may be identified either actively by, for example, scanning by a clinician or passively by, for example, wireless or optical detection of the administration set. As with the fluid supply, once identified, an interaction record may be generated identifying the administration set and one or more of the clinician, programming module, pump, administration set positioning (e.g., administration location (e.g., left forearm, right upper-arm, etc.).

A separate infusion pump 22, 24, 26, and 28 may be used to infuse each of the fluids of the fluid supplies into the patient. The infusion pumps are flow control devices that will act on the respective tube or fluid conduit of the fluid administration set to move the fluid from the fluid supply through the conduit to the patient 48. Because individual pumps are used, each can be individually set to the pumping or operating parameters required for infusing the particular medical fluid from the respective fluid supply into the patient at the particular rate prescribed for that fluid by the clinician. The activities performed by the pump or clinician to infuse the particular medical fluid may be associated with one or interaction which may be recorded and processed as described.

Typically, medical fluid administration sets have more parts than are shown in FIG. 4. Many have check valves, drip chambers, valved ports, connectors, and other devices well known to those skilled in the art. These other devices have not been included in the drawings so as to preserve clarity of illustration.

Figure 5:
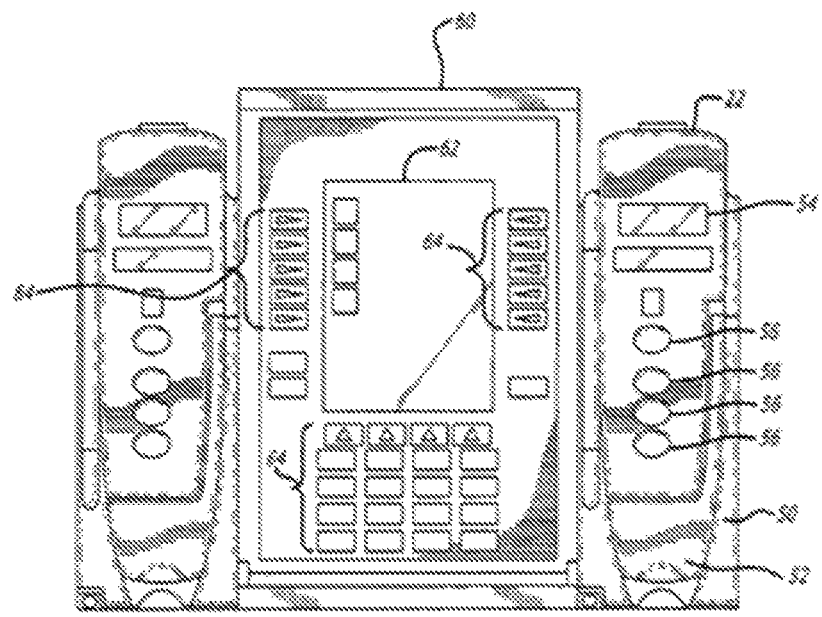
FIG. 5 is a closer view of a portion of the medical device shown in FIG. 4.

FIG. 5 is a closer view of a portion of the medical device shown in FIG. 4. FIG. 5 shows two of the fluid infusion pumps mounted at either side of a programming module, and the displays and control keys of each, with the programming module being capable of programming both infusion pumps. The pump 22 includes a door 50 and a handle 52 that operates to lock the door in a closed position for operation and to unlock and open the door for access to the internal pumping and sensing mechanisms and to load administration sets for the pump. When the door 50 is open, the tube can be connected with the pump 22. When the door 50 is closed, the tube is brought into operating engagement with the pumping mechanism, the upstream and downstream pressure sensors, and the other equipment of the pump. In some implementations, a display 54, such as an LED display, may be located in plain view on the door, and may be used to visually communicate various information relevant to the pump 22, such as alert indications (e.g., alarm messages). Control keys 56 exist for programming and controlling operations of the infusion pump as desired. In some implementations, the control keys may be omitted and be presented as interactive elements on the display 54 (e.g., touchscreen display). The infusion pump 24 also includes audio alarm equipment in the form of a speaker (not shown).

In the example shown in FIG. 4, a programming module 60 is attached to the left side of the infusion pump 24. Other devices or modules, including another infusion pump, may be attached to the right side of the infusion pump 24, as shown in FIG. 4. In such a system, each attached pump represents a pump channel of the overall medical device 20. In some implementations, the programming module is used to provide an interface between the infusion pump 24 and external devices as well as to provide most of the operator interface for the infusion pump 24. Attention is directed to U.S. Pat. No. 5,713,856 entitled "Modular Patient Care System" to Eggers et al. incorporated herein by reference in which the programming module is described as an advanced interface unit.

Returning to FIG. 5, the programming module 60 includes a display 62 for visually communicating various information, such as the operating parameters of the pump 24 and alert indications and alarm messages. The programming module 60 may also include a speaker to provide audible alarms. The programming module 60 may also include one or more input devices, such as control keys 64 or a bar code scanner (not shown) for scanning information relating to the infusion, the patient, the clinician, or other. In some implementations, the display 62 may be implemented as a touchscreen display (e.g., display 312). In such implementations, the control keys 64 may be omitted or reduced in number by providing corresponding interactive elements via a graphical user interface presented via the display 62. The programming module 60 may include a communications system (not shown) with which the programming module 60 may communicate with external equipment such as a medical facility server or other computer and with a portable processor, such as a handheld communication device or a laptop-type of computer, or other information device that a clinician may have to transfer information as well as to download drug libraries to a programming module 60 or pump. The communication module may be used to transfer access and interaction information for clinicians encountering the programming module or device coupled therewith (e.g., pump 22 or bar code scanner). The communications system may include one or more of a radio frequency (RF) system such as an RFID system, an optical system such as infrared, a BLUETOOTH™ system, or other wired or wireless system. The bar code scanner and communications system may alternatively be included integrally with the infusion pump 24, such as in cases where a programming module is not used, or in addition to one with the programming module 60. Further, information input devices need not be hard-wired to medical instruments, information may be transferred through a wireless connection as well.

The example shown in FIG. 5 includes a second pump module 26 connected to the programming module 60. As shown in FIG. 4, more pump modules may be connected. Additionally, other types of modules may be connected to the pump modules or to the programming module such as syringe pump module, oximeter reader module, patient controlled analgesic module, or the like. Each module may generate interaction records of one or more interaction types. The interaction record may include an identifier of the module or device with which the interaction was conducted. The identifier may include a device type identifier, a model or series identifier, or a unique identifier for a specific device.

Figure 6:
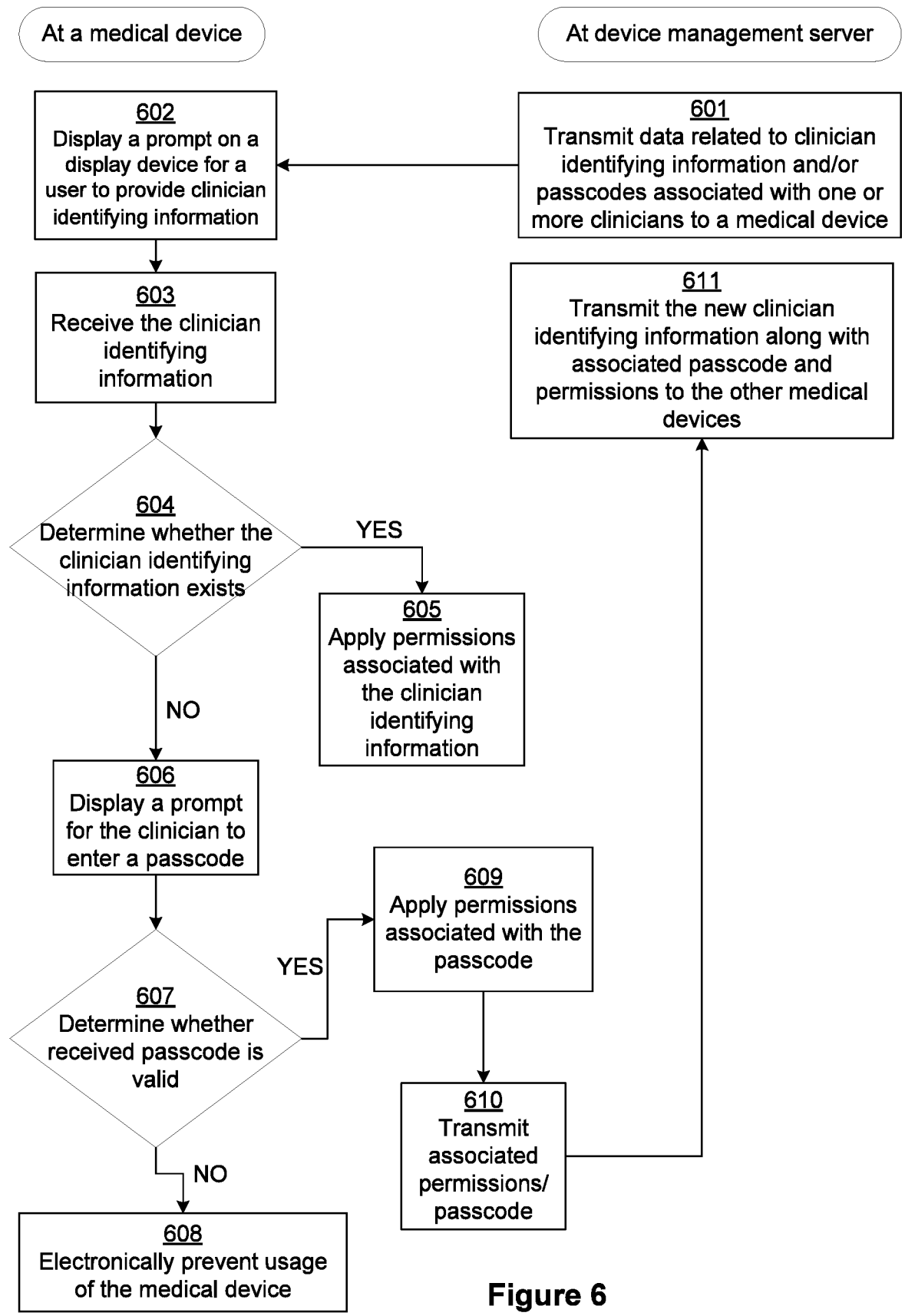
FIG. 6 is a flow chart of an example process of registering a clinician via a medical device and granting or denying access to the medical device, according to illustrative implementations.

Turning now to FIG. 6, there is shown a flowchart illustrating a process of registering a clinician via a medical device and granting or denying access to the medical device. For the purpose of illustrating a clear example, components of the network architecture 100, shown and described with reference to FIG. 1A, components shown and described with reference to FIG. 1B, components of the device management server 108, shown and described with reference to FIG. 2, and components of the medical devices 104, shown and described with reference to FIGS. 3, 4, and 5 may be used to describe the process of registering a clinician via a medical device and granting or denying access to the medical device.

The method 600 includes transmitting, by a processor 202 of the device management server 108, data related to clinician identifying information and/or passcodes associated with one or more clinicians to a medical device 104 (block 601). As described above, examples of clinician identifying information of a clinician may include, but are not limited to, a badge identifier, a passcode, identifiers in different health and/or administration systems (e.g., EMR system), and the like associated with the clinician. As described above, the device management server 108 may store clinician identifying information and/or passcodes of one or more clinicians with permissions for one or more functions of a medical device. The device management server 108 may transmit permissions data associated with the passcodes to the medical device 104. The medical device 104 displays a prompt on a display device for a user to provide clinician identifying information (block 602). For example, the processor 302 of the medical device 104 may display a prompt on a display device associated with the medical device 104 (e.g., display 62) for the user to scan a badge of the user near an RFID reader of the medical device. The medical device 104 receives the clinician identifying information (block 603). The processor 302 of the medical device 104 may receive, via the RFID reader of the medical device 104, clinician identifying information from an RFID tag (e.g., a badge or identification card of a clinician).

The medical device 104 may be configured to determine whether the received clinician identifying information exists (block 604). In some implementations the medical device 104 may determine whether the received clinician identifying information exists by providing the clinician identifying information to the device management server 108 and receive confirmation that the clinician associated with the identifying information is valid, active, and/or in good standing (e.g., clinician is not suspended). As described above, for example, with reference to FIG. 1B, the device management server 108 may receive data related to clinician identifying information of various clinicians, such as data related to badge identifiers ("badge identifier data"), passcodes ("passcode data"), clinician identifiers in different administration and/or health systems (e.g., an EMR system), and the like, of the various clinicians, along with permissions associated with the clinician identifying information for different clinicians.

For example, the medical device 104 may receive a badge identifier of the clinician as the clinician identifying information and may determine whether the received badge identifier exists by providing the badge identifier to the device management server 108 (or medical device 104). The device management server 108 may search for the badge identifier in the badge identifier data stored in one or more data storage units associated with the device management server 108, and provide a confirmation message to the medical device 104 indicating whether the badge identifier is valid, active and/or in good standing based on the search results.

In some implementations, the device management server 108, in response to determining that the clinician identifying information received from the medical device 104 is valid, active, and/or in good standing, may be configured to identify the permissions associated with it and transmit them to the medical device 104 to ensure that the medical device 104 comprises the most current permissions data. The medical device 104 may be configured to update stored permissions data for a clinician with the permissions data most recently received from the device management server 108.

If the medical device 104 determines that the received clinician identifying information exists (YES' at block 604), then the method 600 proceeds to block 605. The medical device 104 applies the one or more permissions associated with the clinician identifying information and transmits a message to the device management server 108 indicating whether the clinician is granted access to the medical device 104 (block 605). As described above, in some implementations, permissions associated with clinician identifying information may indicate whether the clinician has permission to unlock the device, whether the permission to unlock the device was changed based on the clinician's low performance score, whether the clinician requires a second clinician to also provide their clinician identifying information to grant access to the device, whether the clinician has permissions to access certain restricted functions, and the like. If the medical device 104 determines that the received clinician identifying information does not exist (NO' at block 604), then the method 600 proceeds to block 606.

The processor 302 of the medical device 104 displays a prompt for the clinician to enter a passcode on a display device associated with the medical device 104 (block 606). The processor 302 may receive a passcode provided by the clinician, and the processor 302 determines whether the passcode is valid (block 607). The processor 302 may be configured to determine whether the passcode is valid based on whether the passcode is found in the list of passcodes received from the device management server 108. For example, if the processor 302 is unable to find the passcode in the list of received passcodes, then the processor 302 determines that the passcode is not valid. If the processor 302 determines that the passcode is not valid, then the method 600 proceeds to block 608. The processor 302 electronically prevents the clinician from using the medical device (block 608). The processor 302 may be configured to electronically prevent the clinician from using the medical device 104 by preventing the clinician to log into the medical device 104, denying access to the functions of the medical device 104 and/or module(s) connected to the medical device 104 to the clinician, electronically locking the medical device 104, and/or electronically disabling the medical device 104. In some implementations, the processor 302 may disable functions of any modules connected to the medical device 104. For example, the processor 302 may stop or prevent initiation of any infusion of medication to a patient via a pump module connected to the medical device 104 after the medical device 104 is electronically locked out and/or electronically disabled.

The processor 302 may cause the medical device 104 to be in an electronically locked and/or disabled state until the medical device 104 receives clinician identifying information associated with a permissions for one or more functions of the medical device 104. For example, the processor 302 may place the medical device 104 in an electronically locked and/or disabled state until the processor 302 receives badge information and/or passcode of a clinician with permission to unlock the medical device 104 or is granted electronic access to use the medical device 104. Returning to block 607, if the processor 302 determines that the passcode is valid (e.g., identifies the passcode in the list of received passcodes), then the method 600 proceeds to block 609. The processor 302 applies the permissions associated with the passcode (block 609). The processor 302 grants access to the medical device 104 based on the permissions associated with the passcode. The processor 302 may associate the permissions associated with the passcode and the passcode to the clinician identifying information (e.g., badge identifier of the clinician) received in block 604 and transmits the clinician identifying information, the associated passcode, and the associated permissions to the device management server 108 (block 610). The processor 202 of the device management server 108 transmits the new clinician identifying information along with associated passcode and permissions to the other medical devices 104 (block 611). In some implementations, the processor 202 may transmit the new clinician identifying information along with associated passcode and permissions to other medical devices 104 in multiple healthcare facilities of a healthcare organization. The processor 202 may store the new clinician identifying information in association with the associated passcode and permissions in one or more data storage units associated with the device management server 108.

With the device management server 108 transmitting the new clinician identifying information along with associated permissions to other medical devices 104 of the healthcare facility and/or organization, the device management server 108 ensures that the medical devices 104 are updated with the most current clinician identifying information and associated permissions. Thus, a clinician, registered by one medical device 104, is recognized at other medical devices 104 without having to register at the other medical devices 104. The permissions granted and/or updated for the clinician are also applied at the other medical devices 104, thus providing the similar access and/or functionality to the clinician. For example, if a clinician who is registered by a first medical device 104, provides his/her clinician identifying information to a second medical device 104, such as by scanning his/her badge at a second medical device 104, then the second medical 104 may determine that the clinician identifying information exists, is valid, active, and/or in good standing based on the corresponding clinician identifying information received from the device management server 108, and apply the permissions associated with the clinician identifying information based on the corresponding permissions data received from the device management server 108. The second medical device 104 may be configured to utilize the techniques described above with reference to blocks 604 and 605 to determine whether the clinician identifying information exists, is valid, active, and/or in good standing, and apply the associated permissions.

In some implementations, operating parameters and/or preferences may be associated with one or more clinicians (e.g., associated with corresponding clinician identifying information). Examples of the operating parameters and/or preferences may include, but are not limited to, modifications made by the clinician to user interfaces and/or workflows associated with one or more medications frequently administered by the clinician, and the like. In such implementations, the device management server 108 may provide the operating parameters associated with the clinician to the medical devices 104, and the processors 302 of the medical devices 104 may be configured to update display devices associated with the medical devices 104 based on the associated operating parameters. For example, for a medication that is identified as a frequently administered medication, the processor 302 may modify an associated user interface based on the one or more operating parameters and/or preferences indicating the modifications to the user interface previously made by the clinician while administering the medication.

As described above, in some implementations, a medical device 104 may be configured to receive an identifier of a clinician in a patient related system (e.g., an EMR system) of the healthcare facility. The processor 302 may be configured to determine whether that identifier of the clinician (e.g., identifier of the clinician in the EMR) exists in one or more data storage units associated with the medical device 104. If the identifier exists, then processor 302 may apply the permissions associated with the medical device 104. If the processor 302 determines that the identifier does not exist, then the processor 302 may prompt the clinician for other clinician identifying information (e.g., scanning a badge of the clinician) and/or passcodes of the clinician to determine whether to grant access to the medical device 104. If the processor 302 determines that valid clinician identifying information and/or passcodes were provided, then the processor 302 may apply the associated permissions and transmit information related to the identifier of the clinician in the patient related system to the device management server 108, and the device management server 108 may automatically update other medical devices 104 with the identifier of the clinician in the patient related system and associated permissions, passcodes, and/or other clinician identifying information.

With the other medical devices 104 receiving the identifier of the clinician in the patient related system and associated permissions, the clinician is now recognized by the other medical devices 104. Therefore, permissions associated with an identifier of the clinician in the patient related system at one medical device 104 may be applied by another medical device 104 that receives the identifier of the clinician in the patient related system. For example, if a patient associated with a second medical device 104 is under the care of the clinician, and the second medical device 104 receives the corresponding identifier of the clinician in the EMR system, then the second medical device 104 may be configured to apply the permissions associated with the identifier of the clinician, without registering the identifier of the clinician in the EMR system at the second medical device 104.

Figure 7:
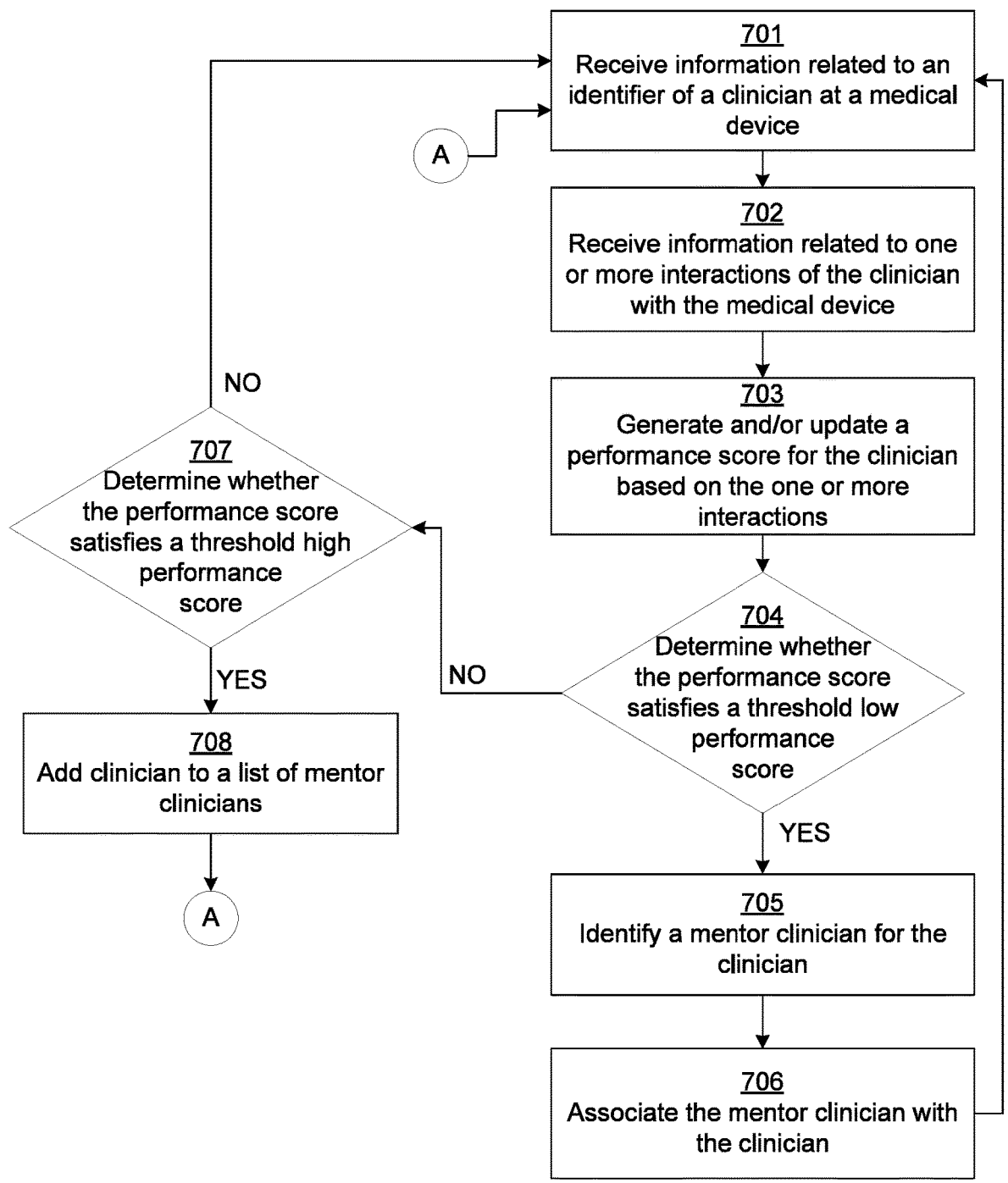
FIG. 7 is a flow chart of an example process of determining a performance score for one or more clinicians in healthcare facility, according to illustrative implementations.

Turning now to FIG. 7, there is shown a flowchart illustrating a process of determining a performance score for one or more clinicians in a healthcare facility. For the purpose of illustrating a clear example, components of the network architecture 100, shown and described with reference to FIG. 1A, components shown and described with reference to FIG. 1B, components of the device management server 108, shown and described with reference to FIG. 2, and components of the medical devices 104, shown and described with reference to FIGS. 3, 4, and 5 may be used to describe the process of determining a performance score for one or more clinicians in a healthcare facility.

The method 700 includes receiving, by the processor 202 of the device management server 108, information related to an identifier of a clinician at a medical device 104 (block 701). As described above, the processor 202 may receive information related to an identifier of a clinician in response to the clinician attempting to access a medical device 104 (e.g., by scanning his or her identification card at the medical device 104). The processor 202 receives information related to the one or more interactions of the clinician with the medical device (block 702). As described above, examples of the information related to interactions of the clinician with a medical device 104 include, but are not limited to, administration of two or more medications concurrently, medication-to-medication interactions of concurrently administered medications, volume of a medication administered, dosage of a medication administered, care area in which the clinician interacted with the medical device, class of medication administered, type of patients to whom medication administered, response time to one or more alarms generated by a medical device, medical route (e.g., intravenously, subcutaneous, arterial, epidural, and the like) of administering a medication, type of set (e.g., tubing, syringe, or connections) for an administration of fluid or medication, duration of use of a set for an administration, type of tubing and connections used during infusion, tubing change (e.g., tubing changed in 72 hours, 96 hours, and the like), administration of a certain medication to a patient, volumetric rate of a medication administered (e.g., administering a medication at a rate of 75 milliliters per hour), and other similar information. The interactions may also be associated with a sequence to determine which interactions occurred and an order or timing for the interactions that occurred.

The processor 202 generates and/or updates a performance score for the clinician based on the one or more interactions of the clinician with the medical device (block 703). The device management server 108 may be configured to store a performance score of a clinician in association with the clinician (e.g., in association with the identifier of the clinician) in one or more data storage systems associated with the device management server 108. In some implementations, the processor 202 may be configured to determine whether a performance score is available for the clinician by searching through one or more data storage systems associated with the device management server 108. If the processor 202 retrieves a performance score associated with the clinician, then the processor 202 updates the performance score based on the received information related to the one or more interactions of the clinician. If a performance score is not retrieved, then the processor 202 generates a performance score based on the received information related to the one or more interactions of the clinician and stores the performance score in association with the clinician in one or more data storage systems associated with the device management server 108.

The processor 202 may be configured to generate and/or update a performance score based on whether an interaction of the clinician with the medical device satisfies a set of rules associated with one or more procedures for treating a patient. Examples of the one or more procedures for treating a patient include, but are not limited to, administering a medication to the patient using the medical device, responding to an alarm generated by a medical device connected to the patient, patient follow-up after administering certain medications, patient monitoring, and the like. Examples of a set of rules associated with a procedure may specify a predetermined volumetric rates, pressure rates, dosage, volume, and the like for one or more medications. In some implementations, the set of rules may also specify one or more groups of medications that may be simultaneously or sequentially administered. In some implementations, the set of rules may specify different volumetric rates, pressure rates, dosage rates, and the like for different types of patients (e.g., patients with a heart condition, obese patients, patients with one or more allergies, and the like). In some implementations, the set of rules may further specify the different medical routes (e.g., intravenous, epidural, subcutaneous, other parenteral routes, and the like) of administration via which a medication may be administered.

The processor 202 may determine whether the clinician's interactions with the medical device for a procedure for treating a patient satisfy a corresponding set of rules based on comparing the received information related to the one or more interactions and corresponding values and/or interactions specified by the set of rules. For example, if the clinician administered two medications simultaneously and the set of rules specify one or more sets and/or groups of medications that may be simultaneously administered, then the processor 202, may verify whether both medications are specified as part of a group or a set of medications that can be administered simultaneously. If the processor 202 determines that both medications are not part of a group or set of medications that can be administered simultaneously, then the processor 202 may determine that the clinician's interactions do not satisfy the set of rules for the procedure for administering the medication, and generates and/or adjusts (e.g., reduces) a performance score of the clinician to reflect the clinician's interactions. If the processor 202 determines that both medications are part of a group or set of medications that can be administered simultaneously, then the processor 202 may determine that the clinician's interactions satisfy the set of rules and generates and/or adjusts (e.g., increases) a performance score of the clinician to reflect the clinician's interactions.

In some implementations, a performance score may be determined by identifying the rules applicable to the interactions for a selected period of time. The period of time may be provided as an input. In some implementations, the period of time may be provided as an input via a user interface. In some implementations, the period of time may be specified in a configuration parameter for the device management server 108. The processor 202 may obtain the interactions for the subject(s) over the period of time. The processor 202 may then obtain the applicable rules from the set of rules for that procedure. This filtering can reduce the amount of resources needed to generate the performance scores for the subject(s). Once the applicable rules are obtained, the processor 202 may then assess the interactions by comparing an interaction with an applicable rule. An interaction record may include an interaction type. The interaction type may be used as a key for identifying relevant compliance rules by, for example, matching an identifier for the interaction type to a value specified in or by a rule for a procedure. The interaction record may also include interaction data identifying, for example, the volume programmed, the rate programmed, or other clinician behavior for the interaction. Each rule may contribute a value to a composite performance score.

The processor 202 may be configured to update a performance score by a predetermined adjustment amount. In some implementations, the processor 202 may be configured to determine an amount based on how frequently the clinician's interactions were satisfied corresponding rules over a predetermined period of time. For example, if the clinician administers a medication at an incorrect dosage several times over a period of 30 days, then the processor 202 may decrease the performance score by a greater amount each successive time.

The processor 202 may update and/or maintain the performance score over a career of the clinician by associating the performance score with the identifier of the clinician. In some implementations, the performance score of a clinician may be a cross-product performance score which reflects the clinician performance scores across different medical devices products. For example, the processor 202 may update and/or maintain device specific performance scores of a clinician, where each device specific performance score may be associated with a different medical device product, and the device specific performance score may be based on one or more clinician interactions with the medical device product. In such implementations, the processor 202 may generate, maintain, and/or update an aggregated performance score based on one or more of the device specific performances scores.

The processor 202 determines whether the performance score of the clinician satisfies a threshold low performance score (block 704). The threshold low performance score may be a predetermined performance score that indicates that the clinician needs additional guidance and support to satisfactorily complete one or more procedures in treating a patient. If the processor 202 determines that the performance score does not satisfy the threshold low performance score (e.g., performance score is greater than the threshold low performance score) ('YES' at block 704), then the method 700 proceeds to block 707. The processor 202 determines whether performance score satisfies a threshold high performance score (block 707).

If the processor 202 determines that the performance score does not satisfy a threshold high performance score (e.g., less than the high performance score) (NO' at block 707), then the method 700 proceeds to block 701. If the processor 202 determines that the performance score satisfies the threshold high performance score (e.g., equal to or greater than the high performance score) ('YES' at block 707), then the method 700 proceeds to block 708. The processor 202 adds the clinician to a list of mentor clinicians (block 708). In some implementations, each clinician in the list of mentor clinicians may be associated with a performance score that satisfies the threshold high performance score. The processor 202 may store the list of mentor clinicians in a data structure in one or more data storage systems associated with the device management server 108. In some implementations, the processor 202 may add the clinician to the list of mentor clinicians by adding the identifier of the clinician to the data structure comprising the list of mentor clinicians.

At block 704, if the processor 202 determines that the performance score satisfies the threshold low performance score (e.g., the performance score is equal to or less than the threshold low performance score) ('YES' at block 704), then the method 700 proceeds to block 705. The processor 202 identifies a mentor clinician for the clinician (block 705). In some implementations, the processor 202 identifies a mentor clinician associated with fewest clinicians. The processor 202 associates the mentor clinician with the clinician (block 706). The processor 202 stores the association of the mentor clinician with the clinician in a data storage system associated with the device management server 108.

The device management server 108 may be configured to utilize the performance scores of the clinicians to improve efficiency and performance of other systems of a health care facility that are communicatively coupled to the device management server 108. For example, in some scenarios, a health care facility may utilize external clinician staffing resource centers for temporary or traveling clinicians that can assist the health care facility, and the device management server 108 may be configured to identify one or more high performing external clinician staffing resource centers based on the performance scores of the their clinicians.

Figure 9:
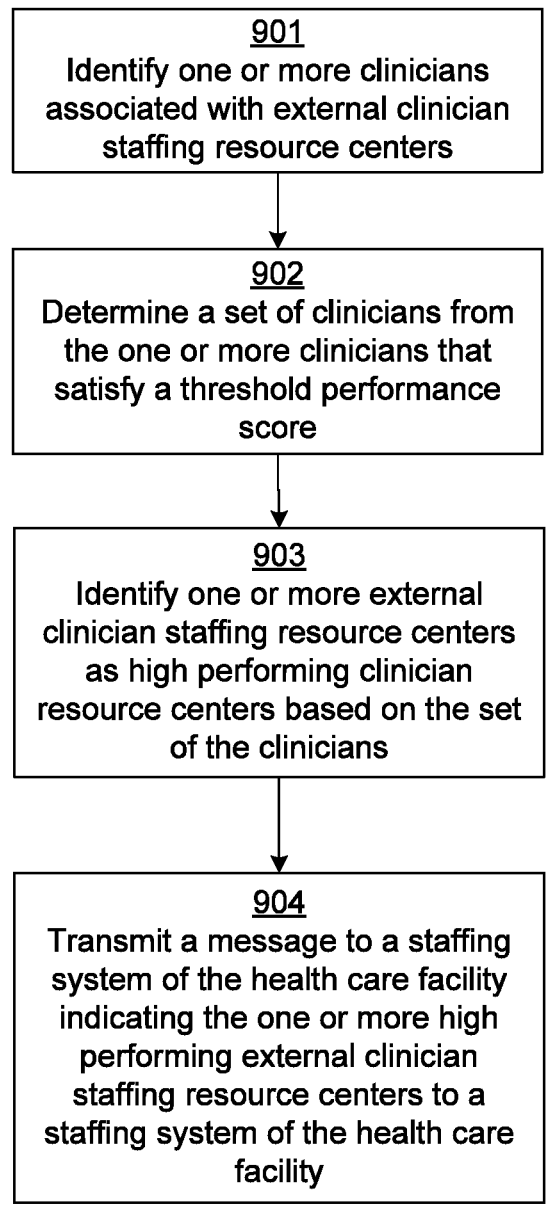
FIG. 9 is a flow chart of an example process of rating and identifying one or more high performing external clinician staffing resource centers, according to illustrative implementations.

Additional details of identifying one or more high performing external clinician staffing resource centers are described herein with reference to FIG. 9. In another example, the device management server 108 may be configured to optimize scheduling of clinicians based on their performance scores and/or a scheduling criteria. Additional details of an optimized scheduling of clinicians are described herein with reference to FIG. 10. In yet another example, the device management server 108 may identify clinicians with low performance scores and generate alerts and/or reminders for a follow-up activity for the clinician to complete. Additional details of generating alerts and/or reminders for follow-up activity for clinicians with low performance scores are described with reference to FIG. 11.

In some implementations, the processor 202 may be configured to identify a set of clinicians with performance scores that satisfy a high threshold performance score for a threshold amount of time (e.g., a number weeks, a consecutive number of months, and the like), as highly regarded clinicians and associate a title (e.g., "Hall of Famer", "M.V.P.", and the like) and/or a graphical icon (e.g., a graphical crown, and the like) with the clinicians and may transmit the association of the titles and/or graphical icons with the clinicians to the medical devices 104. For example, the processor 202 may be configured to identify a set of clinicians with performance scores that satisfy the high threshold performance score for a 5 consecutive months as "Hall of Fame" clinicians and associates the title "Hall of Famer" and a graphical crown icon with corresponding clinician identifying information of the clinicians. In some implementations, a processor 302 of a medical device 104 may be configured to determine whether a clinician requesting access to the medical device 104 is associated with any specific titles (e.g., "Hall of Famer", "M.V.P.", and the like) and/or graphical icons and display the associated titles and/or graphical icons on a display device (e.g., near the name of the clinician) associated with the medical device 104.

In some implementations, the processor 202 may be configured to determine one or more high performing care areas (e.g., intensive care unit, emergency room, ward, and the like) and/or one or more low performing care areas of a healthcare facility based on performance scores of clinicians associated with the care areas. In some implementations, the processor 202 may be configured to display the one or more high performing care areas on one or more display devices positioned on one or more floors of the healthcare facility. In some implementations, the processor 202 may be configured to generate and transmit messages to the clinicians associated with the low performing care areas indicating that their associated care area is a low performing care area. In some implementations, the processor 202 may be configured to identify a set of clinicians with low performance scores for a threshold period of time and/or low performing care areas with a group and associate the set of clinicians and/or the care areas with a group name (e.g., a "Wall of Shame" group name, and the like).

In some implementations, the device management sever 108 may be configured to transmit instructions to the medical devices 104 to electronically lock out from the medical devices 104 and/or deny access to access to one or more features of the medical devices 104 toclinicians with performance scores satisfying the low performance threshold score. In response to receiving the instructions, the medical devices 104 may be configured to not grant access to any functionality (e.g., unlocking the medical device 104) of the medical device to the clinician. In some implementations, the device management server 108 may be configured to associate the clinicians with performance scores satisfying the low performance threshold score with a second clinician (e.g., a mentor clinician) and require the second clinicians to also provide their clinician identifying information in order for the medical device 104 to grant access to the clinicians with low performance scores. In some implementations, the device management server 108 may be configured to compile training packages to address the low performance scores of the clinicians. In some implementations, the device management server 108 may be configured to determine effectiveness of training packages based on changes to the performance scores of clinicians. In some implementations, the device management server 108 may be configured to cause additional safety alerts to be displayed on a display device associated with a medical device and/or modify a workflow in the medical device while a clinician with low performance score is interacting with the medical device to reduce any safety risks. In some implementations, the processor 202 may cause a clinician with a low performance score to be electronically locked out from the medical device 104 and/or deny access to one or more features of a functional module connected to a medical device 104 (e.g., an infusion pump connected to a medical device 104) to prevent the clinician from initiating and/or interfering with administration of medication. Additional details of electronically locking out clinicians from medical devices and/or denying access to one or more features of medical devices, generating and/or compiling training packages, assessing effectiveness of the training, and/or requiring a secondary clinician authorization to access a medical device and/or one or more functions of the medical device are described in U.S. Provisional Patent Application No. 62/865,906, which application is incorporated herein by reference.

Figure 8:
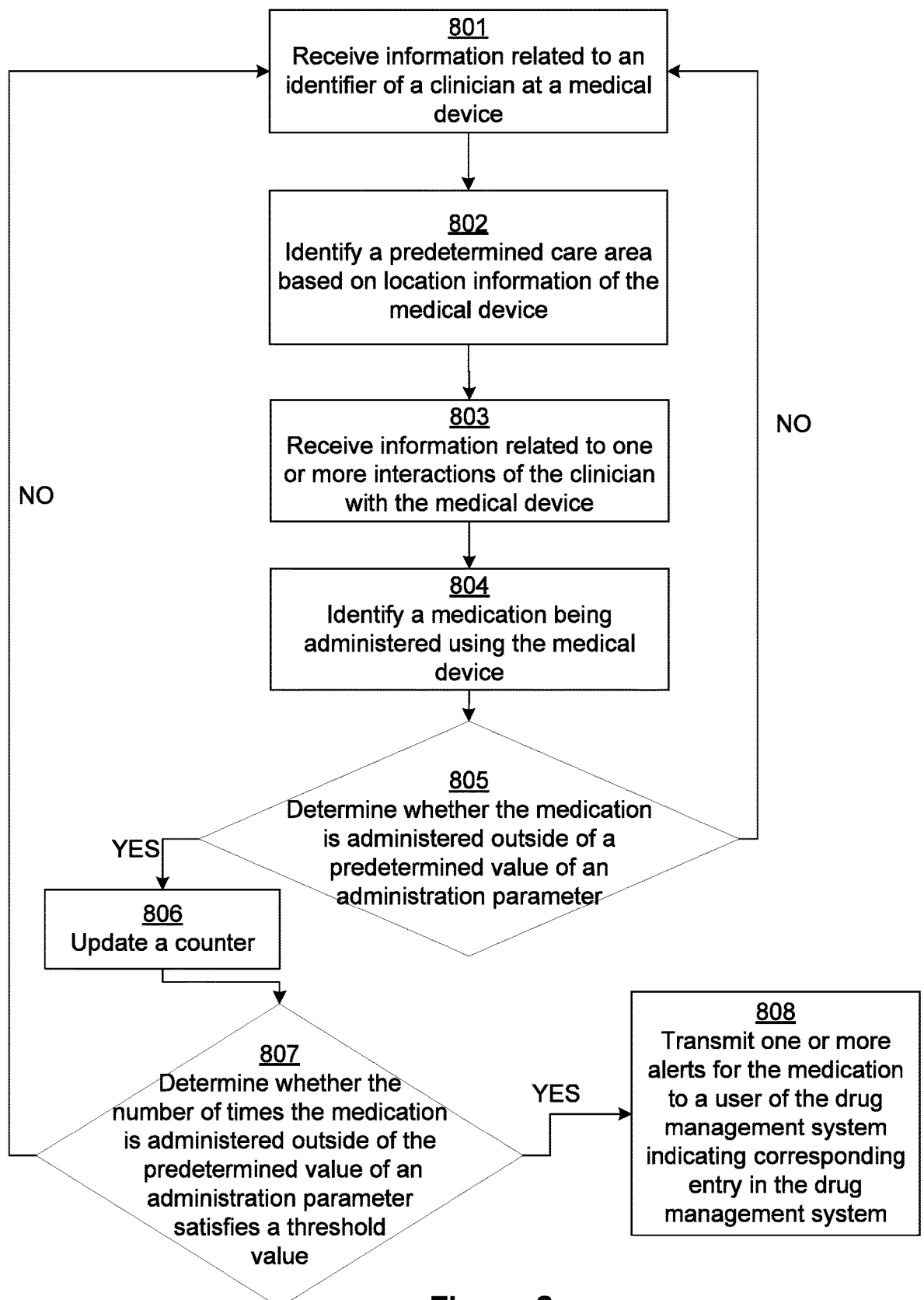
FIG. 8 is a flow chart of an example process of alerting a medication system and/or a pharmacy technician operating parameters of administering medication being overridden and determining whether one or more administration parameters of a medication can be adjusted based on clinician interactions, according to illustrative implementations.

Turning now to FIG. 8, there is shown a flowchart illustrating a process of alerting a medication system and/or a pharmacy technician of healthcare facility of clinicians overriding operating parameters of administering medication and determining whether one or more administration parameters of a medication can be adjusted based on one or more clinicians interactions with a medical device used for administering the medication. For the purpose of illustrating a clear example, components of the network architecture 100, shown and described with reference to FIG. 1A, components shown and described with reference to FIG. 1B, components of the device management server 108, shown and described with reference to FIG. 2, and components of the medical devices 104, shown and described with reference to FIGS. 3, 4, and 5 may be used to describe the process of alerting a medication system and/or a pharmacy technician of healthcare facility of clinicians overriding operating parameters of administering medication and determining whether one or more administration parameters of a medication can be adjusted based on one or more clinicians interactions with a medical device used for administering the medication.

The method 800 includes receiving, by the processor 202 of the device management server 108, information related to an identifier of a clinician at a medical device 104 (block 801). The processor 202 may receive information related to an identifier of a clinician in response to the clinician attempting to access a medical device 104. In some implementations, the clinician may attempt to access a medical device 104 by providing his or her access credentials to the medical device 104 (e.g., scanning his or her identification card at the medical device 104). A clinician's access credentials may be associated with and/or include a unique identifier of the clinician, and the medical device 104 may be configured to transmit the unique identifier associated with the clinician to the device management server 108 in response to successfully granting access to the clinician. Examples of a unique identifier of a clinician include, but are not limited to, a user identifier, an employee identifier, and the like.

The processor 202 identifies a predetermined care area of the healthcare facility based on location information of the medical device (block 802). The location of the medical device may be determined by way of a GPS locator system within the medical device, or by the medical device transmitting over or connecting with a particular WiFi transceiver at a known location. Examples of care area include, but are not limited to, intensive care unit (ICU), ward, and the like. The processor 202 receives information related to the one or more interactions of the clinician with the medical device (block 803). Examples of the information related to interactions of the clinician with a medical device 104 include, but are not limited to, administration of a certain medication to a patient, volumetric rate of a medication administered (e.g., administering a medication at a rate of 105 milliliter per hour), and the like. In some implementations, the processor 202 may group the medical device interactions of the clinician in a group associated with the predetermined care area in which the medical device is located. For example, the processor 202 may group the interactions of the clinician with a medical device located in an intensive care unit in a group associated with the intensive care unit and may group interactions of the clinician with a different medical device located in a ward in a group associated with the ward.

The processor 202 identifies a medication being administered to a patient using the medication device (block 804). In some implementations, the processor 202 may identify the medication based on the one or more interactions of the clinician with the medical device. For example, an interaction of the clinician with the medical device may be to program a medication to be administered to the patient using the medical device, and the information related to the interaction may indicate an identifier and/or name of the medication, and the processor 202 may determine the medication being administered to the patient based on the identifier and/or name of the medication indicated by the information related the interactions. In some implementations, the processor 202 may identify the medication being administered based on the patient's record in an EMR system communicatively coupled to the device management server 108.

The processor 202 determines whether the medication is administered outside a predetermined value of an administration parameter of the medication (block 805). Examples of a medication's administration parameters may include, but are not limited to, dosage of the medication, volumetric rate of a medication administered, administration of two or more medications concurrently, medication-to-medication interactions of concurrently administered medications, volume of a medication administered, a list of medications with which the medication may be concurrently administered, volume of a medication administered, and the like. Predetermined values of a medication's administration parameters may be stored in association with the medication in a data storage system associated with a drug management system. The predetermined values of the medication's administration parameters may be provided as inputs to the drug management system by a user of the drug management system, such as a pharmacist. The device management server 108 may be communicatively coupled to the drug management system. In some implementations, the processor 202 may receive predetermined values of one or more administration parameters of the medication from the medical device and/or the drug management system. In some implementations, the processor 202 may be configured to query the drug management system for predetermined values of one or more of the medication's administration parameters.

The processor 202 may determine one or more administered values of the medication by the clinician based on the received information related to the one or more interactions of the clinician with the medical device. For example, the received information may indicate that the clinician administered the medication at a volumetric rate of the 100 milliliters per hour. The processor 202 may determine whether the medication is administered outside of a predetermined administration parameter value based on a comparison of the administered value with a predetermined value of a corresponding administration parameter. For example, the processor 202 may determine that the medication is administered outside of a predetermined administration parameter value if a volumetric rate at which the medication is administered by the clinician is greater or lesser than the predetermined volumetric rate for that medication.

If the processor 202 determines that the medication is not administered outside a predetermined administration parameter value ('NO' at block 805), then the method 800 proceeds to the block 801. If the processor 202 determines that the medication is administered outside a predetermined administration parameter value ('YES' at block 805), then the method proceeds to block 806. The processor 202 updates a counter (block 806). The counter may be associated with the medication and/or an administration parameter of the medication. The counter may be associated with the predetermined care area. For example, the processor 202 may maintain multiple counters for a single medication and/or an administration parameter of the medication, where each counter may be associated with a different predetermined care area of the healthcare facility. The processor 202 may update the counter by increasing the counter by a predetermined value (e.g., increasing the value by one) to indicate that the medication is administered outside of the predetermined administration parameter value again.

The processor 202 determines whether the number of times the medication is administered outside of the predetermined value of an administration parameter satisfies a threshold value (block 807). The processor 202 may determine whether the threshold value is satisfied based on the value of the counter. If the threshold value is not satisfied ('NO' at block 807), then the method 800 proceeds to block 801. In some implementations the processor 202 may update (e.g., decrease) a score associated with the clinician to indicate that the clinician did not satisfactorily follow expected procedure for administering the medication. If the processor 202 determines that the threshold value is satisfied ('YES' at block 807), then the method 800 proceeds to block 808. In some implementations, if the processor 202 determines that the threshold value is satisfied, the processor 202 may not negatively adjust the performance score of the clinician.

The processor 202 transmits one or more alerts for the medication to a user of the drug management system (block 808). The processor 202 may indicate a corresponding entry in the drug management system of the medication, and/or other information related to the medication's administration in the alert. For example, the processor 202 may include information related to an identifier of the medication in the drug management system, and the clinicians of the predetermined care area that administered the medication outside of the predetermined values. In some implementations, the processor 202 may add the medication to a list of medications that have been administered outside of one or more respective predetermined values of their administration parameters a threshold number of times. The processor 202 may transmit an instruction to the drug management system to cause the drug management system to display a graphical icon on a display device associated with the drug management system, where the graphical icon identifies the list of medications and indicates that these medications are administered outside of the predetermined values most often. In some implementations, the processor 202 may order the list of medications based on the number of times the medication is administered outside a predetermined value (e.g., top 10 medication offenders), and include the ordered list in the alert. In some implementations, if the threshold number of times is not satisfied, then the processor 202 may order a list of clinicians that most frequently administer the medication outside of the predetermined parameters and include that list in the alert to cause that list to be displayed on a display device associated with the medication system.

In some implementations, the processor 202 may determine a new value to a predetermined value of an administration parameter of a medication in the list. The processor 202 may determine the new value for the administration parameter based on the values of the administration parameter at which the medication is administered to the. For example, if a medication is administered at a volumetric rate that is outside the predetermined volumetric rate value (e.g., 100 ml/hour) for the threshold number of times, then the processor 202 may calculate an average (e.g., 105 ml/hour) of the administered volumetric rates and determine the new value of the volumetric rate of the medication as the average (e.g., 105 ml/hour) of the administered volumetric rates, and/or may cause the new value of the volumetric rate to displayed via an editor of a medication system. In some implementations, the processor 202 may determine the new value for only a predetermined care area in which the medication is administered outside of the predetermined value for the administration parameter. For example, if a medication is administered at a volumetric rate that is outside the predetermined volumetric rate value for the threshold number of times in ICU, then the processor 202 may calculate an average of the volumetric rates at which the medication is administered in that ICU, and may determine the new value of the volumetric rate of the medication in that ICU as the average of the administered volumetric rates in that ICU.

The processor 202 may transmit the determined new value to a user of a drug management system in a message indicating the new value as a suggested update to the predetermined value. In some implementations, the processor 202 may indicate in the message that the new value is for a predetermined care area. In some implementations, the processor 202 may display the determined new value in an editor user interface for the various medications stored in a data storage system associated with the drug management system.

Turning now to FIG. 9, there is shown a flowchart illustrating a process of rating and identifying one or more high performing external clinician staffing resource centers. For the purpose of illustrating a clear example, components of the network architecture 100, shown and described with reference to FIG. 1A, components shown and described with reference to FIG. 1B, components of the device management server 108, shown and described with reference to FIG. 2, and components of the medical devices 104, shown and described with reference to FIGS. 3, 4, and 5 may be used to describe the process of identifying one or more high performing external clinician staffing resource centers.

The method 900 includes identifying, by the processor 202 of the device management server 108, one or more clinicians that are associated with external clinician staffing resource centers (block 901). The device management server 108 may receive clinician information from a clinician staffing system of the healthcare facility, and the clinician information may specify external clinician staffing resource centers for the clinicians that are temporarily staffed and/or are traveling clinicians. The processor 202 may store the clinician (e.g., an identifier of the clinician) in association with the corresponding external clinician staffing resource center in a data storage system associated with the device management server 108. The processor 202 may identify the one or more clinicians based on their associations with the external clinician staffing resource centers.

The processor 202 determines a set of clinicians from the one or more clinicians that satisfy a threshold performance score (block 902). As described above, the processor 202 stores the performance score of the clinician in association with the clinician (e.g., identifier of the clinician) in a data storage system. The processor 202 may identify the performance score for each of the one or more clinicians and determine whether the performance score satisfies a threshold performance score (e.g., the performance score is equal to or greater than the threshold performance score). The threshold performance score may be a predetermined performance score specified by healthcare facility. If the performance score of a clinician satisfies a threshold performance score, then the processor 202 may add the clinician to a set of clinicians.

The processor 202 identifies one or more external clinician staffing resource centers as high performing clinician resource centers based on the set of the clinicians (block 903). The processor 202 may identify one or more external clinician staffing resource centers with a threshold number of clinicians in the determined set, and identify them as the one or more external clinician staffing resource centers. For example, the threshold number may be predetermined to be 3, and the processor 202 may group the clinicians in the set based on their associated external clinician staffing resource centers, and identify the external clinician staffing resource centers with at least 3 clinicians. In some implementations, the processor 202 may be configured to identify one or more clinicians with the highest performance score, and identify their associated external clinician staffing resource centers as high performing external clinician staffing resource centers. In some implementations, the processor 202 may be configured to generate a rating for each of the one or more external clinician staffing resource centers based on the number of clinicians with performance scores satisfying the threshold performance score and associated with the resource center.

The processor 202 may transmit a message to a staffing system of the health care facility indicating the one or more high performing external clinician staffing resource centers to a staffing system of the health care facility (block 904). In some implementations, the processor 202 may cause the staffing system to request clinician(s) from the one or more the high performing external clinician staffing resource centers in response to transmitting the message to the staffing system.

Figure 10:
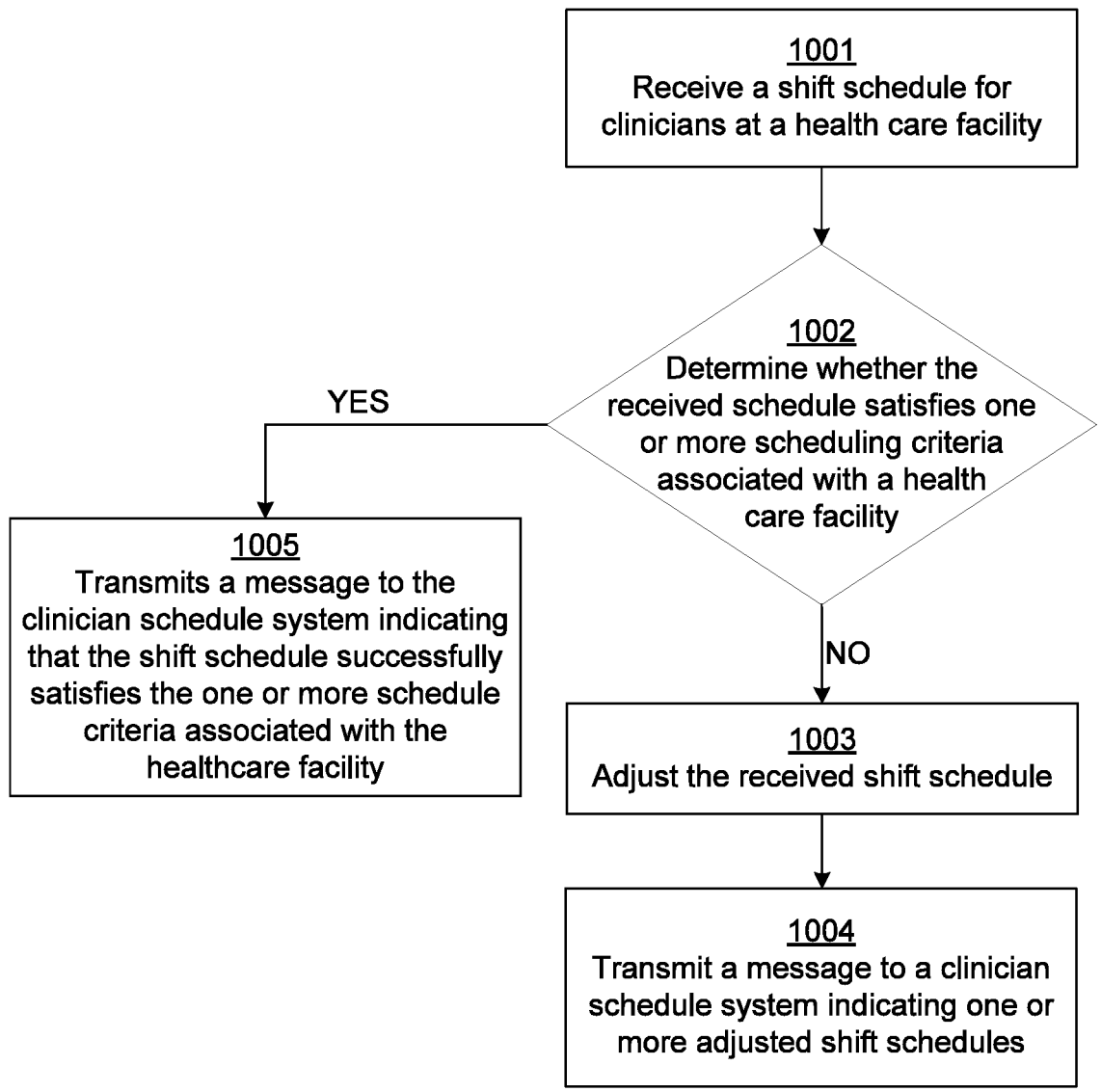
FIG. 10 is a flow chart of an example process of verifying and/or optimizing a schedule for clinicians, according to illustrative implementations.

Turning now to FIG. 10, there is shown a flowchart illustrating a process of verifying and/or optimizing a shift schedule for clinicians. For the purpose of illustrating a clear example, components of the network architecture 100, shown and described with reference to FIG. 1A, components shown and described with reference to FIG. 1B, components of the device management server 108, shown and described with reference to FIG. 2, and components of the medical devices 104, shown and described with reference to FIGS. 3, 4, and 5 may be used to describe the process of an optimized scheduling of clinicians.

The method 1000 includes receiving, by the processor 202 of the device management server 108, a shift schedule for clinicians at a health care facility (block 1001). In some implementations, the performance scores of the clinicians in the shift schedule may be received. The processor 202 determines whether the received shift schedule satisfies one or more scheduling criteria associated with a health care facility (block 1002). The device management server 108 may be configured to receive one or more scheduling criteria for a health care facility, and the processor 202 may store the received scheduling criteria in association with the health care facility. The processor 202 may be configured to verify and/or optimize the received shift schedule based on the scheduling criteria associated with the health care facility. In some implementations, a scheduling criteria may indicate a ratio of clinicians with non-low performance scores to clinicians with low performance scores. For example, a scheduling criteria may indicate that 3 clinicians with non-low performance scores should be scheduled for every 2 clinicians with low performance scores that are scheduled.

In some implementations, the processor 202 may be configured to apply a scheduling criteria based on the time of the shift. For example, the processor 202 may be configured to apply a scheduling criteria indicating 2 clinicians with non-low performance scores for every 2 clinicians with low performance scores for a night shift and a scheduling criteria indicating 4 clinicians with non-low performance scores for every 2 clinicians with low performance score for an afternoon shift. The processor 202 may identify the performance scores for the clinicians included in the received shift schedule and, based on the performance scores of the clinicians, determine if the ratio of clinicians with non-low performance scores to clinicians with low performance scores included in the shift schedule satisfies the indicated ratio of the scheduling criteria. If the ratio is satisfied, then the processor 202 may determine that the received shift schedule satisfies that scheduling criteria.

In some implementations, a scheduling criteria indicates a threshold average performance score for a shift based on the performance scores of the clinicians scheduled for the shift. The processor 202 may calculate an average performance score based on the performance scores associated with the clinicians included in the received shift schedule, and may determine that such a scheduling criteria is satisfied if the calculated average performance satisfies the indicated threshold average performance score, then the processor 202 may determine that the received shift schedule satisfies such a scheduling criteria. In some implementations, a scheduling criteria may indicate a threshold deviation between the performance scores of the clinicians included in a shift schedule to achieve even distribution of performance scores across different shifts at the health care facility. The processor 202 may be configured to determine whether the shift schedule satisfies this scheduling criteria based on whether differences between the performance scores of the clinicians included in the shift schedule satisfy the threshold deviation.

If the processor 202 determines that the received shift schedule does not satisfy one or more scheduling criteria associated with the healthcare facility ('NO' at block 1002), then the method 1000 proceeds to block 1003. The processor 202 adjusts the received shift schedule (block 1003). The processor 202 may be configured to adjust the received shift schedule by swapping one or more clinicians included in the shift schedule with one or more other clinicians currently not scheduled for that shift and/or a shift during the same time period as the time period of the shift associated with the received shift schedule. For example, the processor 202 may adjust the received shift schedule and/or generate a new shift schedule by replacing a first clinician with a performance score not satisfying a threshold performance score specified in a scheduling criteria in the received shift schedule with a second clinician not scheduled during the same time period as the time period of the shift of the received shift schedule, based on the performance score of the second clinician satisfying the specified threshold performance score. In some implementations, the processor 202 may electronically prevent the first clinician from using one or more medical devices during the time period of the shift of the received shift schedule.

In some implementations, the processor 202 may be configured to swap for one or more clinicians scheduled for a different shift. In some implementations, the processor 202 may swap for one or more clinicians scheduled for a shift that has not yet started. The processor 202 may be configured to continue to swap one or more clinicians between different shifts until schedules of each shift satisfy the one or more scheduling criteria associated with the health care facility. The processor 202 may be configured to store the one or more adjusted schedules in a data storage system associated with the device management server 108. The processor 202 transmits a message to a clinician schedule system indicating one or more adjusted schedules (block 1004). The processor 202 may include an instruction in the message to cause the clinician schedule system to update the corresponding schedules of the adjusted schedules in the clinician schedule system.

Returning now to block 1002, if the processor 202 determines that the received shift schedule satisfies the one or more scheduling criteria associated with the healthcare facility ('YES' at block 1002), then the method 1000 proceeds to block 1005. The processor 202 transmits a message to the clinician schedule system indicating that the shift schedule successfully satisfies the one or more scheduling criteria associated with the healthcare facility (block 1005).

In some implementations, the processor 202 may be configured to cause the schedule of the clinicians to be displayed on display devices of the medical devices 104. For example, the processor 202 may identify, based on the verified and/or the optimized schedule, patients associated with each clinician and the medical devices 104 associated with patients. The processor 202 may transmit information related to the clinician's schedule (e.g., information related to when the clinician's shift starts and ends) to the medical device 104 for the clinician's shift schedule to be displayed on the display device of the medical device 104. In some implementations, the processor 202 may be configured to transmit the verified and/or optimized schedule to be displayed on a display device associated with the clinician scheduling system.

Figure 11:
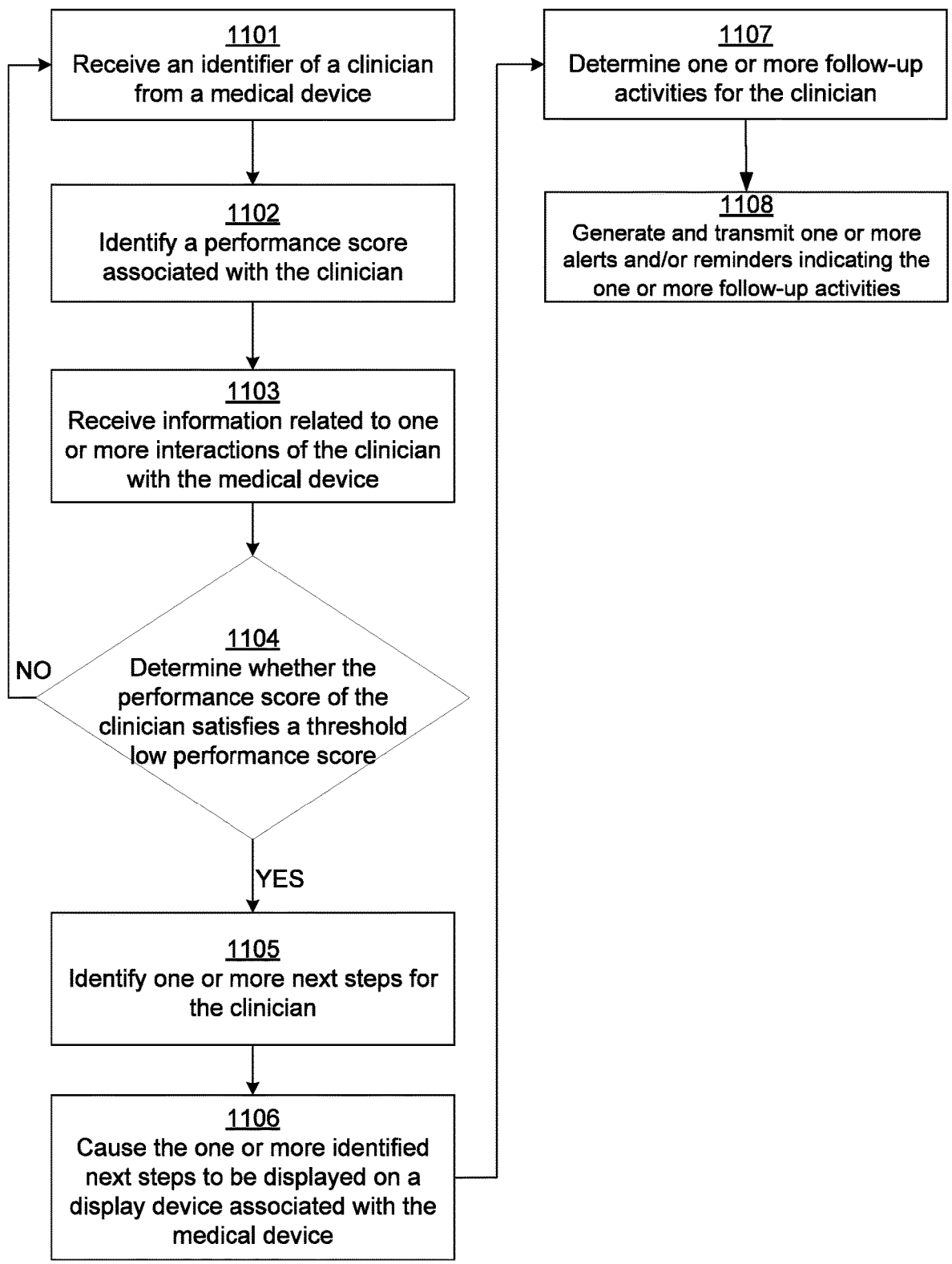
FIG. 11 is flow chart of an example process of identifying workflows and generating alerts and/or reminders for follow-up activity for clinicians with low performance scores, according to illustrative implementations.

Turning now to FIG. 11, there is shown a flowchart illustrating a process of identifying workflows and generating alerts and/or reminders for follow-up activity for clinicians with low performance scores. For the purpose of illustrating a clear example, components of the network architecture 100, shown and described with reference to FIG. 1A, components shown and described with reference to FIG. 1B, components of the device management server 108, shown and described with reference to FIG. 2, and components of the medical devices 104, shown and described with reference to FIGS. 3, 4, and 5 may be used to describe the process of generating alerts and/or reminders for follow-up activity for clinicians with low performance scores.

The method 1100 includes receiving, by the processor 202 of the device management server 108, an identifier of a clinician from a medical device (block 1101). As described above, in some implementations, the processor 202 may receive the identifier of the clinician after the clinician is granted access to the medical device. The processor 202 identifies a performance score associated with the clinician (block 1102). As described above, a performance score of the clinician may be stored in association with the clinician (e.g., identifier of the clinician) in a data storage system associated with the device management server 108, and the processor 202 identifies the performance score based on information related to the clinician and/or the received identifier of the clinician.

The processor 202 receives information related to one or more interactions of the clinician with the medical device (block 1103). The processor 202 determines whether the performance score of the clinician satisfies a threshold low performance score (block 1104). If the processor 202 determines that the performance score of the clinician does not satisfy the threshold low performance score ('NO' at block 1104), then the method 1100 terminates. If the processor 202 determines that the performance score of the clinician satisfies threshold the threshold low performance score ('YES' at block 1104), then the method 1100 proceeds to block 1105.

The processor 202 identifies one or more next steps for the clinician (block 1105). The processor 202 may be configured to identify one or more next steps for the clinicians based on a stored set of rules that specify one or more next steps in the different workflows with which the medical device is configured. In some implementations, the processor 202 may be configured to identify an appropriate next step in a workflow based on a last completed step and/or a current step in the workflow. In some implementations, the processor 202 may identify the last completed step and/or a current step in the workflow, based on the received information related to the one or more interactions with the medical device by the clinician. For example, if the received information related to the one or more interactions indicate that the last step completed by the clinician is selection of infusion of a medication, then the processor 202 may identify that the next step is checking a setting in the medical device based on the one or more next steps specified by the stored set of rules for the infusion workflow for that medical device.

The processor 202 causes the one or more identified next steps to be displayed on a display device associated with the medical device (block 1106). In some implementations, the processor 202 may transmit the one or more identified next steps and an instruction to display the one or more transmitted next steps to the medical device to cause the medical device to display the one or more next steps on a display device associated with the medical device. In some implementations, the medical device may be configured to display graphical items (e.g., alert boxes, message boxes, and the like) associated with the steps in a workflow with which the medical device is configured, and the processor 202 may transmit a message and/or an instruction indicating identifiers associated with the identified next step(s) to cause a processor of the medical device (e.g., processor 302) to identify the next step(s) in the stored steps for the workflow and display them on a display device associated with the medical device using the associated graphical items.

The processor 202 determines one or more follow-up activities for the clinician (block 1107). Examples of follow-up activities include, but are not limited to, checking one or more settings and/or configuration data for a medical device, checking operational errors of the medical device, checking vital signs of the patient, and the like. The processor 202 may determine the one or more follow-up activities based on the one or more identified next steps. For example, if an identified next step is to provide an input to start an infusion of a medication, then the processor 202 may determine a follow-up activity of confirming an operational status of a pump module connected to the medical device after a predetermined amount of time. In some implementations, the processor 202 may determine the one or more follow-up activities based on the information related to the one or more interactions of the clinician with the medical device. For example, if the information related to the one or more interactions of the clinician with the medical device indicate that a patient associated with the medical device is disconnected from the medical device, then the processor 202 may determine a follow-up activity of confirming that a record of the patient in an EMR system accurately indicates the time at which the clinician is disconnected from the medical device.

The processor 202 generates and transmits one or more alerts and/or reminders indicating the one or more determined follow-up activities to the clinician and/or other computing systems of the health care facility that are communicatively coupled to the device management server 108 (block 1108). In some implementations, the processor 202 may be configured to transmit an alert and/or reminder for a determined follow-up activity based on whether the determined follow-up activity includes performing one or more tasks in a computing system of the health care facility. If the processor 202 determines that the follow-up activity includes performing one or more tasks in a computing system, then the processor 202 may transmit the alert and/or reminder to the computing system to cause the alert and/or reminder to be displayed on a display device of the computing system. For example, if the follow-up activity includes updating a patient record in an EMR system of the healthcare facility, then the processor 202 may transmit an alert and/or reminder for the follow-up activity to the EMR and cause the alert and/or reminder to be displayed in response to the clinician accessing the EMR. In some implementations, the processor 202 may transmit the one or more alerts and/or reminders to a computing device associated with a clinician (e.g., mobile device of the clinician) to provide the one or more alerts and/or reminders to the clinician. In some implementations, the processor 202 may be configured to lock the clinician out of the medical devices 104 if the clinician does complete one or more tasks of the follow-up activity within a predetermined threshold of time (e.g., within 3 hours) associated with the follow-up activity.

Figure 12:
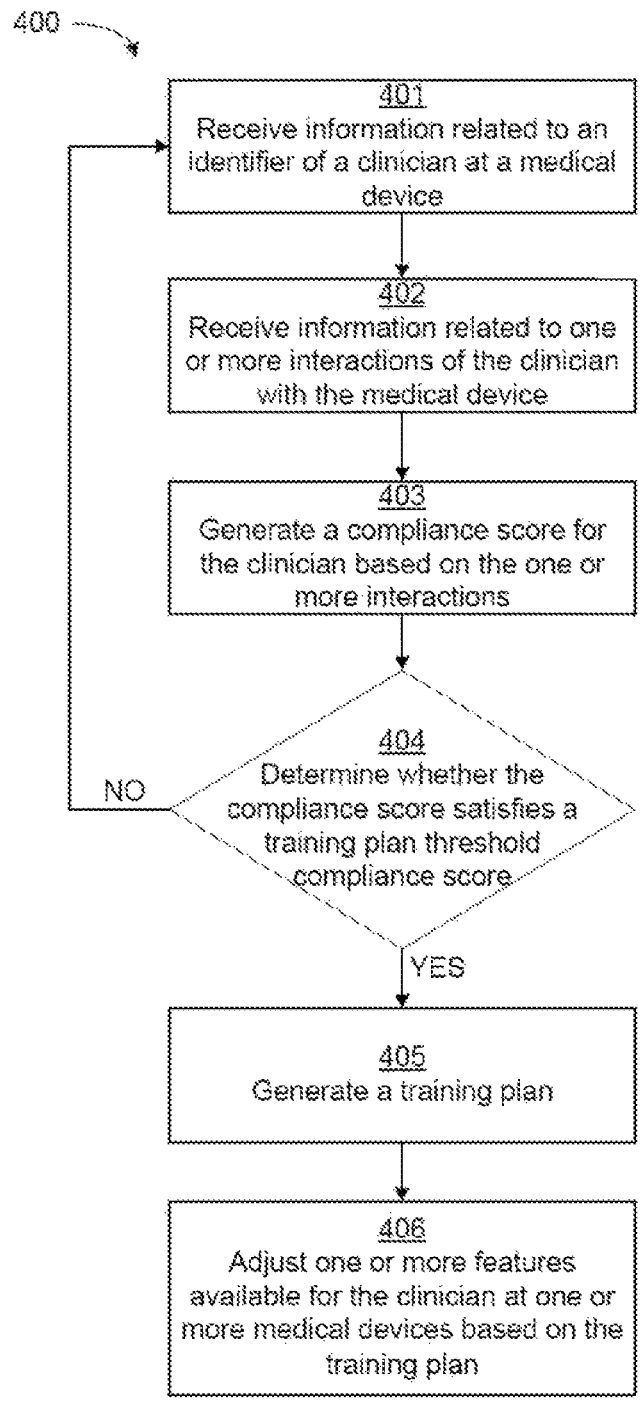
FIG. 12 is a flow chart of an example process of determining non-compliance patters of a clinician according to illustrative implementations.

Turning now to FIG. 12, there is a shown flowchart illustrating a process of determining a compliance score and generating a training plan for a clinician. For the purpose of illustrating a clear example, components of the network architecture 100, shown and described with reference to FIG. 1, components of the device management server 108, shown and described with reference to FIG. 2, and components of the medical devices 104, shown and described with reference to FIG. 3, may be used to describe the process determining a compliance score and generating a training plan for a clinician.

The method 400 includes receiving, by the processor 202 of the device management server 108 information related to an identifier of a clinician at a medical device 104 (block 401). The processor 202 may receive information related to an identifier of a clinician in response to the clinician attempting to access a medical device 104. In some implementations, the clinician may attempt to access a medical device 104 by providing his or her access credentials to the medical device 104 (e.g., scanning his or her identification card at the medical device 104). A clinician's access credentials may be associated with and/or include a unique identifier of the clinician, and the medical device 104 may be configured to transmit the unique identifier associated with the clinician to the device management server 108 in response to receiving the clinician's access credentials and/or a unique identifier. Examples of a unique identifier of a clinician include, but are not limited to, a user identifier, an employee identifier, and the like. In some implementations, the processor 202 may determine whether to grant access to the clinician for the medical device 104 based on whether the clinician requires a secondary authorization for the clinician.

The processor 202 receives information related to one or more interactions of the clinician with the medical device (block 402). Examples of the information related to interactions of the clinician with a medical device 104 include, but are not limited to, administration of a certain medication to a patient, volumetric rate of a medication administered (e.g., administering a medication at a rate of 5 milliliter per hour), administration of two or more medications concurrently, medication-to-medication interactions of concurrently administered medications, volume of a medication administered, dosage of a medication administered, care area in which the clinician interacted with the medical device, class of medication administered, type of patients to whom medication administered, response time to one or more alarms generated by a medical device, medical route (e.g., intravenously, subcutaneous, arterial, epidural, and the like) of administering a medication, type of set (e.g., tubing, syringe, or connections) for an administration of fluid or medication, duration of use of a set for an administration, type of tubing and connections used during infusion, tubing change parameters (e.g., tubing changed in 72 hours, 96 hours, and the like), and other similar information. The interactions may also be associated with a sequence to determine which interactions occurred and an order or timing for the interactions that occurred.

The processor 202 generates a compliance score for the clinician based on the one or more interactions (block 403). The processor 202 may be configured to generate a compliance score based on whether an interaction is compliant with one or more protocols. In some implementations, the processor 202 may determine whether an interaction is compliant based on a stored set of rules that indicate or specify one or more corresponding compliant interactions. For example, the set of rules may specify compliant volumetric rates for one or more medications. Similarly, the set of rules may specify one or more of pressure rates, dosage, volume, set type, and the like. In some implementations, the set of rules may specify one or more compliant parameters for one or more medications, types of patients, care areas within a health care facility, class of medications, and the like. The set of rules may also specify one or more groups of medications that may be simultaneously or sequentially administered. In some implementations, the set of rules may specify different compliant volumetric rates, pressure rates, dosage rates, and the like for different types of patients (e.g., patients with a heart condition, obese patients, patients with one or more allergies, and the like). The set of rules may further specify the different medical routes of administration via which a medication may be administered. Examples of medical routes of administration include, but are not limited to, intravenous, epidural, subcutaneous, other parenteral routes, and the like.

The processor 202 may compare the information related to the one or more received interactions and corresponding compliant interactions specified by the set of rules to determine whether the interactions are compliant. For example, if the clinician administered two medications simultaneously and the set of rules specify one or more sets and/or groups of medications that may be simultaneously administered, then the processor 202, may verify whether both medications are specified as part of a group or a set of medications that can be administered simultaneously. If the processor 202 determines that both medications are not part of a group or set of medications that can be administered simultaneously, then the processor 202 may determine that the clinician's interactions are non-compliant and generates and/or adjusts (e.g., reduces) a compliance score of the clinician to reflect the clinician's non-compliant interactions. If the processor 202 determines that both medications are part of a group or set of medications that can be administered simultaneously, then the processor 202 may determine that the clinician's interactions are compliant and generates and/or adjusts (e.g., increases) a compliance score of the clinician to reflect the clinician's compliant interactions.

A compliance score may be determined by identifying the rules applicable to the interactions for a selected period of time. In an interactive implementation, the period of time may be selected via user interface. In an unattended implementation, such as a periodic compliance reporting engine, the period of time may be specified as a configuration parameter of the reporting engine. The processor 202 may obtain the interactions for the subject(s) over the period of time. The processor 202 may then obtain the applicable compliance rules from the set of compliance rules. This filtering can reduce the amount of resources needed to generate the compliance scores for the subject(s). Once the applicable compliance rules are obtained, the processor 202 may then assess the interactions by comparing an interaction with an applicable rule. An interaction record may include an interaction type. The interaction type may be used as a key for identifying relevant compliance rules by, for example, matching an identifier for the interaction type to a value specified in or by a compliance rule. The interaction record may also include interaction data identifying, for example, the volume programmed, the rate programmed, or other clinician behavior for the interaction. Each rule may contribute a value to a composite compliance score. The rules may be normalized to a risk scale whereby a first limit is associated with safe or compliant behavior and a second limit is associated with unsafe or non-compliant behavior. This normalization allows each rule to contribute equally to a composite score.

Equation (1) provides one example expression for generating a composite compliance score. Some implementations may include a weighting factor to allow certain rules or interactions to contribute more or less heavily to a compliance score. A weighting factor may be specified for all scores or may be adjusted for specific clinician or groups of clinicians to emphasize or deemphasize performance of certain activities.

$$\sum_{i=0}^{n} \sum_{r=0}^{x} \omega_{ri} s_r(i) \qquad \text{Equation 1}$$

where
  n is the number of interactions;
  x is the number of rules applicable to a given interaction (i);
  ω is a weighting factor for a given rule (r) or interaction (i); and
  sr is a scoring function for the given rule (r) as applied to the data from the interaction (i).

In some implementations, the processor 202 may be configured to compare the information related to the one or more interactions of one clinician with interactions of other clinicians and determine whether the one or more interactions of one clinician is compliant. For example, for a first clinician, if the processor 202 receives information related to an interaction indicating that the first clinician administered a medication at a pressure rate, then the processor 202 may compare whether the pressure rate at which the first clinician administered the medication is outside of a range of pressure rates used by a majority of other clinicians. If the processor 202 determines that the pressure rate is outside of a range of pressure rates, then the processor 202 may determine that the interaction of the first clinician is non-compliant. Similarly, if the processor 202 determines that the pressures is not outside of a range of pressure rates, then the processor 202 may determine that the interaction of the first clinician is compliant.

The processor 202 may be configured to adjust a compliance score by a predetermined adjustment amount. In some implementations, the processor 202 may be configured to determine an adjust amount based on how frequently the clinician's interactions were non-compliant over a predetermined period of time. For example, if the clinician administers a medication at an incorrect dosage several times over a period of 30 days, then the processor 202 may decrease a compliance score by a greater amount every time the clinician administered the medication at incorrect dosages. In some implementations, each clinician may be associated with a default starting compliance score, and the processor 202 may store the compliance score in association with an identifier of the clinician. The processor 202 may update and/or maintain the compliance score over a career of the clinician.

In some implementations, the processor 202 may group and/or categorize the clinician interactions into predetermined groups and/or categories based on a predetermined set of rules. For example, the processor 202 may group and/or categorize interactions related to administering a medication at a dosage as one group and/or category of interactions, may group and/or categorize interactions related to administering a medication at a volumetric rate as a second group and/or category of interactions, may group and/or categorize interactions related to administering multiple medications simultaneously as a third group and/or category of interactions. The processor 202 may generate and/or associate a compliance score for each group and/or category of interactions. In some implementations, the processor 220 may generate an overall compliance score based on the compliance scores of one or more groups and/or categories of interactions.

The processor 202 determines whether the compliance score satisfies a training plan threshold compliance score (block 404). A training plan threshold compliance score may be a predetermined threshold compliance score. The threshold compliance score may be specified as a system-wide configurable value. In some implementations, the configurable value may be specified via a user interface. In some implementations, the threshold compliance score may be dynamically generated such as for specific clinicians or group of clinicians. In some implementations, the processor 202 may be configured to determine that the compliance score satisfies the training plan threshold compliance score if the compliance score is corresponds to the training plan threshold compliance score. In some implementations, if the compliance score is equal to or greater than a training plan threshold compliance score, then the processor 202 may be configured to determine that the compliance score satisfies the training plan threshold compliance score.

If the processor 202 determines that the compliance score does not satisfy the threshold compliance score (e.g., the clinician or clinicians are deemed compliant), then the method 400 proceeds to block 401. If the processor 202 determines that the compliance score satisfies the threshold compliance score (e.g., the clinician or clinicians are deemed out of compliance), then the method 400 proceeds to block 405. The processor 202 generates a training plan (block 405). The processor 202 may identify training modules associated with the one or more interactions and/or category of the one or more interactions. For example, if the one or more non-compliant interactions are associated with a category of administering a medication at a volumetric rate, then the processor 202 may identify training modules associated with that category. In some implementations, one or more training modules may be associated with one or more training videos, and the processor 202 may compile the one or more training videos into a software package and associate the package with the training plan. In some implementations, the processor 202 may request and/or receive key stroke and/or touch input data from medical devices configured to receive key stroke and/or touch input, and the processor 202 may associate the received key stroke and/or touch input data with the training videos and/or training plan. In some implementations, the processor 202 may generate one or more videos based one the key stroke and/or touch input data and provide them to the clinician for a visual feedback of the clinician's interactions with the medical device.

The processor 202 may specify one or more training tasks in the training plan. The one or more training tasks may specify instructions and/or tasks for the clinician to perform to complete the training plan. The training tasks may specify training materials for the clinician to review and/or tests to verify that the clinician reviewed the training materials, training videos to review, and the like. In some implementations, the processor 202 may determine whether the clinician completed a training plan based on whether the clinician completed the training tasks. The processor 202 may transmit the training plan to the clinician. In some implementations, the processor 202 may store the training plan in association with the clinician's identifier and transmit a message comprising a link to the training plan to the clinician.

In some implementations, the processor 202 may associate the clinician with a secondary authorization from other clinicians that have a higher compliance score than the clinician. For example, the processor 202 may identify clinicians with compliance scores equal to or above a certain threshold compliance score, and associate one or more of the identified clinicians as secondary authorization for the clinician. By associating one or more other clinicians as secondary authorization for the clinician, the processor 202 causes the medical device to display a prompt for the one or more other clinicians to login or access the medical device while the clinician is accessing the medical device.

The processor 202 may adjust one or more features available for the clinician at one or more medical devices based on the training plan (block 406). In response to determining that the clinician is granted access to the medical device, the processor 202 may cause the medical device to display additional prompts or messages to the clinician based on the generated training plan. For example, the processor 202 may transmit a training video associated with the training plan to the medical device and cause the medical device to display the training video in response to the clinician being granted access to the medical device. The processor 202 may cause the medical device to display different training videos associated with the training plan at different steps of an interaction. For example, if the clinician is administering a medication intravenously, then the processor 202 may instruct the medical device to display a first video of the training that instructs the user to verify if the medication can be administered intravenously and provide a prompt to the clinician to confirm that the medication can be administered intravenously. In response to receiving a confirmation from the clinician, the processor 202 may cause the medical device to display a second video that instructs the clinician to verify if the dosage of the medication is suitable for that particular patient.

In some implementations, the processor 202 disable certain features for the clinician at one or more medical devices based on the training plan. For example, the processor 202 may disable features that can allow a seasoned clinician to skip a few intermediate steps, and cause the clinician associated with the training plan to perform additional steps (e.g., checking labels and confirming labels are checked), which a clinician with a higher compliance score may not have to perform. In some implementations, the processor 202 may lock the clinician out of one or more medical devices until the processor 202 determines that the clinician has successfully completed the training plan. A medical device may include an idle time lock out value. Once a clinician accesses the medical device, if no interactions are detected with the medical device for a period of time, the clinician may be deemed idle. This absence of activity may be recorded as an interaction with the medical device and processed as described. The period time used to assess idleness may be dynamically adjusted. For example, a clinician having a low compliance score may have a higher idle time than a clinician with a higher compliance score. This may encourage the low performing clinician to take their time while interacting with the medical device. The lower threshold for the more competent clinician may improve security of the medical device. The period of time may be further generated based on the drug to be delivered, type of infusion, administration set, or other detectable property of the medication delivery.

The processor 202 may monitor and/or track the training plan to determine whether the clinician has completed one or more tasks of the training plan. In some implementations, in response to determining that one or more tasks of the training plan are completed, the processor 202 may enable one or more features associated with the training tasks. In some implementations, the processor 202 may grant access to one or more medical devices to the clinician if a threshold number of training tasks are completed.

The processor 202 may control additional or alternative aspects of the medical device based on competence score. For example, the medical device may dynamically require secondary review for an activity based on the competence score of the clinician initiating the activity. For example, if a controlled substance is to be delivered via a medical device and the clinician's competence score is below a threshold, the medical device may prevent initiation of the delivery until confirmed by a second clinician. In some implementations, the medical device may be configured to receive confirmation from a second clinician having a competence score greater than the first clinician or greater than a threshold. The threshold may be associated with the medical device, drug, care area for the clinician, or a standard competency threshold. Additional or alternative factors that may be used to configure the medical device for secondary review include the infusion type, the number of channels running for a programming module, differences between an order and actual programmed parameters (e.g., more deviations from provided programming parameters can indicate a higher probability of clinician error), administration set type (e.g., some sets require specific priming or may be prone to loading errors), patient characteristic (e.g., a patient has specific medical condition, needs, etc.).

In some implementations, the medical device may be configured to require a specific clinician to review and approve an interaction. For example, a nursing manager's confirmation may be required to initiate a program entered by a junior nurse. As another example, a specific physician's confirmation may be required to initiate a program for an experimental drug or therapy (e.g., as part of a clinical trial). The identity may be confirmed by activating a credentialing system to receive identifying information for the secondary reviewer. For example, the medical device may scan a badge associated with the secondary reviewer. The scan may provide an identifier for the secondary reviewer which can then be used to confirm identity, competence score, or other factor to assess whether the individual can review the work of the initiating clinician. An attempt and result (e.g., authorized, rejected) of a particular secondary reviewer may be stored as an interaction and included in the processing described herein.

The compliance score described thus far is generally associated with a clinician. In some implementations, the compliance score may be generated for devices. In some cases, it may be that the device, not the clinician, needs attention. In such implementations, interactions with a specific device, model or series of device, or device type may be identified and scored. Based on the compliance score, one or more control signals may be transmitted to a device identified to be out of compliance. The control signal may adjust one or more features of the device such as disabling the login or adjusting the power status (e.g., sleep mode or turn off). In some implementations, the control signal may adjust a user interface or other perceivable feedback element to indicate the device may not be properly functioning. In some implementations, the control signal may be transmitted to a technician or other automated troubleshooting system to initiate maintenance on the device. The maintenance may include executing a remote diagnostic process or system refresh to identify or correct deficiencies with the device.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software, or any combination thereof.

With further reference to FIG. 1-12, the system of the subject technology may identify one or more interactions of a first user with one or more medical devices, and determine, based on the one or more interactions and a predetermined set of rules, a compliance score associated with the first user. In response to the compliance score not satisfying a threshold compliance score, the system may reduce an access level of the first user to at least one of the one or more medical devices and generating a training program associated with the at least one medical device and the one or more interactions. In this regard, reducing the access level may include reducing a number of respective features of the at least one medical device that are available to the first user. The system is configured to then, without user involvement, automatically compile and/or send a training package associated with the training program to the first user and notify the first user to complete the training program using the training package.

The system may then (at a later time) receive a request for the first user to access the at least one medical device. For example, the first user may attempt to log in to the medical device (e.g., swipe his or her badge). The system may then determine, responsive to the request, that the first user has not completed the training program, and require authorization from a second user authorized to use the at least one medical device before granting the request for the first user to access the at least one medical device. According to various implementations, the training program may be generated based on a category associated with the one or more interactions and includes one or more training tasks associated with the number of respective features of the at least one medical device. In some implementations, the system may determine that the first user completed the training program, including the one or more training tasks, and restore, responsive to determining that the first user completed the training program, the access level of the first user with regard to the at least one medical device. In some implementations, each of the one or more respective features of the medical device are made available to the first user as a corresponding training task associated with each feature is completed by the first user.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method comprising: tracking one or more interactions of a first user with one or more medical devices; determining, based on a set of stored rules and the one or more interactions, a compliance score; determining whether the compliance score satisfies a threshold compliance score; in response to determining that the compliance score satisfies the threshold compliance score, generating, based on the one or more interactions, a training plan for the first user; and adjusting, based on the training plan, one or more features of the one or more medical devices available for the first user at the one or more medical devices.

Clause 2. The method of Clause 1, further comprising: receiving a request for access to a medical device of the one or more medical devices, wherein the request is associated with an identifier of the first user; determining whether an identifier of a second user from a plurality of users is granted access to the medical device; and in response to determining that the identifier of the second user is granted access to the medical device, granting the identifier of the first user access to the medical device.

Clause 3. The method of Clause 2, wherein the identifier of the second user is associated as secondary authorization for the identifier of the first user.

Clause 4. The method of Clause 3, wherein determining whether the identifier of the second user is granted access to the medical device, further comprises: in response to receiving the request for access from the first user, providing for display on a display device associated with the medical device a request for credentials associated with the identifier of the second user; receiving credentials associated with the identifier of the second user; and granting the identifier of the second user access to the medical device.

Clause 5. The method Clause 3, wherein a compliance score of the second user is greater than the compliance score of the first user.

Clause 6. The method of Clause 1, wherein generating, based on the one or more interactions, the training plan for the first user further comprises: determining, based on the one or more interactions, a category associated with the one or more interactions; identifying, based on the category, one or more training modules; and generating, based on the one or more training modules, the training plan.

Clause 7. The method of Clause 6, wherein the training plan comprises one or more training tasks corresponding to the one or more training modules and the features of the one or more medical devices.

Clause 8. The method of Clause 7, further comprising: determining whether a training task of the one or more training tasks of the training plan is completed; and in response to determining that the training task is completed, granting access to a corresponding feature of the medical device to the first user.

Clause 9. The method of Clause 1, wherein adjusting, based on the training plan, the one or more features of the one or more medical devices available for the first user at the one or more medical devices further comprises: providing a training video associated with the one or more features for display on a display device associated with one of the one or more medical devices.

Clause 10. The method of Clause 1, further comprising: locking out the first user from the one or more medical devices; receiving a request to access the one or more medical devices by the first user; in response to receiving the request, determining whether the first user completed the training plan; and in response to determining that the first user completed the training plan, granting access to the first user for the one or more medical devices.

Clause 11. A system comprising: a memory storing instructions; and one or more processors coupled with the memory and configured to execute the instructions to cause the system to: track one or more interactions of a first user with one or more medical devices; determine, based on a set of stored rules and the one or more interactions, a compliance score; determine whether the compliance score satisfies a threshold compliance score; when the compliance score satisfies the threshold compliance score, generate, based on the one or more interactions, a training plan for the first user; and adjust, based on the training plan, one or more features of the one or more medical devices available for the first user at the one or more medical devices.

Clause 12. The system of Clause 11, wherein the one or more processors are configured to execute instructions to cause the system to: receive a request for access to a medical device of the one or more medical devices, wherein the request is associated with an identifier of the first user; determine whether an identifier of a second user from a plurality of users is granted access to the medical device; and when the identifier of the second user is granted access to the medical device, granting the identifier of the first user access to the medical device.

Clause 13. The system of Clause 12, wherein the identifier of the second user is associated as secondary authorization for the identifier of the first user.

Clause 14. The system of Clause 13, wherein the one or more processors are configured to execute instructions to cause the system to: when the request for access from the first user is received, provide for display on a display device associated with the medical device a request for credentials associated with the identifier of the second user; receive credentials associated with the identifier of the second user; and grant the identifier of the second user access to the medical device.

Clause 15. The system of Clause 13, wherein a compliance score of the second user is greater than the compliance score of the first user.

Clause 16. The system of Clause 11, wherein the one or more processors are configured to execute instructions to cause the system to: determine, based on the one or more interactions, a category associated with the one or more interactions; identify, based on the category, one or more training modules; and generate, based on the one or more training modules, the training plan.

Clause 17. The system of Clause 16, wherein the training plan comprises one or more training tasks corresponding to the one or more training modules and the features of the one or more medical devices.

Clause 18. The system of Clause 17, wherein the one or more processors are configured to execute instructions to cause the system to: determine whether a training task of the one or more training tasks of the training plan is completed; and when the training task is completed, granting access to a corresponding feature of the medical device to the first user.

Clause 19. The system of Clause 11, wherein the one or more processors are configured to execute instructions to cause the system to: provide a training video associated with the one or more features for display on a display device associated with one of the one or more medical devices.

Clause 20. The system of Clause 11, wherein the one or more processors are configured to execute instructions to cause the system to: lock out the first user from the one or more medical devices; receive a request to access the one or more medical devices by the first user; when the request is received, determine whether the first user completed the training plan; and when the first user has completed the training plan, grant access to the first user for the one or more medical devices.

Clause 21. A method comprising: identifying interactions of a plurality of clinicians with one or more medical devices; generating, based on a set of stored rules and one or more interactions of each user of the plurality of clinicians, a performance score for each of plurality of clinicians; receiving a first shift schedule associated with the plurality of clinicians; determining whether the first shift schedule satisfies one or more scheduling criteria associated with a healthcare facility; in response to determining that the first shift schedule does not satisfy the one or more scheduling criteria and a first performance score for a first clinician not satisfying a first evaluation threshold of the one or more scheduling criteria: (1) generating a new second shift schedule for the plurality of clinicians that replaces a first clinician scheduled during a first time period with a second clinician not currently scheduled during the time period based on a second performance score of the second clinician, and (2) electronically preventing the first clinician from using at least one of the one or more medical devices during the first time period; and causing the new schedule for the shift to be displayed on a display device associated with a clinician scheduling system.

Clause 22. The method of Clause 21, further comprising: identifying, based on performance scores of a subset of the plurality of clinicians, one or more high performing resource centers; generating a request for one or more clinicians not among the plurality of clinicians from the one or more high performing resource centers; and transmitting the request to the clinician scheduling system.

Clause 23. The method of Clause 21, further comprising: determining a subset of the plurality of clinicians whose performance scores satisfy a threshold low performance score; receiving information related to interactions of a clinician of the subset with a medical device; identifying, based on the information, a workflow initiated at the medical device; identifying, based on the workflow and the set of stored rules, a next step in the workflow; and causing the next step to be displayed on a display device associated with medical device.

Clause 24. The method of Clause 23, further comprising: determining, based on the information related to the one or more interactions, one or more follow-up activities for the clinician; generating an alert for the one or more follow-up activities; and transmitting the alert for the one or more follow-up activities to a computing device associated with the clinician.

Clause 25. The method of Clause 24, further comprising: determining, based on the one or more follow-up activities, whether an update to an electronic record of a patient at an administration system of the healthcare facility is required; and in response to determining that an update to the electronic record is required, causing the alert to be displayed adjacent to the electronic record on a display device associated with to the administration system.

Clause 26. The method of Clause 21, further comprising: receiving information related to a set of interactions of a clinician of the plurality of clinicians with a medical device; identifying a predetermined care area of the medical device based on location information of the medical device; determining, based on the information, a parameter value associated with a medication administered to a patient; in response to determining that the parameter value is outside of a predetermined threshold value, updating a medication counter associated with the predetermined care area, wherein the medication counter indicates a number of times the medication is administered using a parameter value outside of the predetermined threshold value; determining whether the medication counter satisfies a second threshold value; and in response to determining that the medication counter satisfies the second threshold value, causing an alert identifying the medication and the predetermined care area to be displayed on a display device of a drug management system.

Clause 27. The method of Clause 26, further comprising: in response to determining that the counter satisfies the threshold value, calculating, based at least on the value for the parameter of the medication at which the medication is administered, a new value for the parameter; and transmitting an alert to a user of the drug management system to update a current value of the parameter to the new value for the parameter.

Clause 28. The method of Clause 26, further comprising: in response to determining that the medication counter does not satisfy the second threshold value, reducing the performance score of the clinician by a predetermined amount; determining whether the reduced performance score satisfies a predetermined threshold low performance score; and in response to determining that the reduced performance score satisfies the predetermined threshold low performance score, updating permissions of associated with the clinician to electronically prevent the clinician from using the one or more medical devices.

Clause 29. The method of Clause 26, further comprising: in response to determining that the reduced performance score satisfies a predetermined threshold low performance score, assigning a training package to the clinician; determining whether the training package is successfully completed; and in response to determining that the training package is successfully completed, electronically granting access to the clinician to use the one or more medical devices.

Clause 30. The method of Clause 26, further comprising: in response to determining that the reduced performance score satisfies a predetermined threshold low performance score, assigning a mentor clinician to the clinician; and electronically preventing the clinician from using a medical device among the one or more medical devices until clinician identifying information associated with the mentor clinician is received.

Clause 31. A system comprising: a memory storing instructions; and one or more processors coupled with the memory and configured to execute the instructions to cause the system to: identify interactions of a plurality of clinicians with one or more medical devices; generate, based on a set of stored rules and one or more interactions of each user of the plurality of clinicians, a performance score for each of plurality of clinicians; receive a first shift schedule associated with the plurality of clinicians; determine whether the first shift schedule satisfies one or more scheduling criteria associated with a healthcare facility; when the first shift schedule does not satisfy the one or more scheduling criteria and a first performance score for a first clinician not satisfying a first evaluation threshold of the one or more scheduling criteria: (1) generate a new second shift schedule for the plurality of clinicians that replaces a first clinician scheduled during a first time period with a second clinician not currently scheduled during the time period based on a second performance score of the second clinician, and (2) electronically prevent the first clinician from using at least one of the one or more medical devices during the first time period; and cause the new schedule for the shift to be displayed on a display device associated with a clinician scheduling system.

Clause 32. The system of Clause 31, wherein the one or more processors are configured to execute instructions to cause the system to: identify, based on performance scores of a subset of the plurality of clinicians, one or more high performing resource centers; generate a request for one or more clinicians not among the plurality of clinicians from the one or more high performing resource centers; and transmit the request to the clinician scheduling system.

Clause 33. The system of Clause 31, wherein the one or more processors are configured to execute instructions to cause the system to: determine a subset of the plurality of clinicians whose performance scores satisfy a threshold low performance score; receive information related to interactions of a clinician of the subset with a medical device; identify, based on the information, a workflow initiated at the medical device; identify, based on the workflow and the set of stored rules, a next step in the workflow; and cause the next step to be displayed on a display device associated with medical device.

Clause 34. The system of Clause 33, wherein the one or more processors are configured to execute instructions to cause the system to: determine, based on the information related to the one or more interactions, one or more follow-up activities for the clinician; generate an alert for the one or more follow-up activities; and transmit the alert for the one or more follow-up activities to a computing device associated with the clinician.

Clause 35. The system of Clause 34, wherein the one or more processors are configured to execute instructions to cause the system to: determine, based on the one or more follow-up activities, whether an update to an electronic record of a patient at an administration system of a healthcare facility is required; and when an update to the electronic record is required, cause the alert to be displayed adjacent to the electronic record on a display device associated with to the administration system.

Clause 36. The system of Clause 31, wherein the one or more processors are configured to execute instructions to cause the system to: receive information related to a set of interactions of a clinician of the plurality of clinicians with a medical device; identify a predetermined care area of the medical device based on location information of the medical device; determine, based on the information, a parameter value associated with a medication administered to a patient; when the parameter value is outside of a predetermined threshold value, update a medication counter associated with the predetermined care area, wherein the medication counter indicates a number of times the medication is administered using a parameter value outside of the predetermined threshold value; determine whether the medication counter satisfies a second threshold value; and when the medication counter satisfies the second threshold value, causing an alert identifying the medication and the predetermined care area to be displayed on a display device of a drug management system.

Clause 37. The system of Clause 36, wherein the one or more processors are configured to execute instructions to cause the system to: when the counter satisfies the threshold value, calculate, based at least on the value for the parameter of the medication at which the medication is administered, a new value for the parameter; and transmit an alert to a user of the drug management system to update a current value of the parameter to the new value for the parameter.

Clause 38. The system of Clause 36, wherein the one or more processors are configured to execute instructions to cause the system to: when the medication counter does not satisfy the second threshold value, reducing the performance score of the clinician by a predetermined amount; determine whether the reduced performance score satisfies a predetermined threshold low performance score; and when the reduced performance score satisfies the predetermined threshold low performance score, updating permissions of associated with the clinician to electronically prevent the clinician from using the one or more medical devices.

Clause 39. The system of Clause 36, wherein the one or more processors are configured to execute instructions to cause the system to: when the reduced performance score satisfies a predetermined threshold low performance score, assign a training package to the clinician; determine whether the training package is successfully completed; and when the training package is successfully completed, electronically grant access to the clinician to use the one or more medical devices.

Clause 40. The system of Clause 36, wherein the one or more processors are configured to execute instructions to cause the system to: determine that the reduced performance score satisfies the predetermined threshold low performance score, assigning a mentor clinician to the clinician; and electronically prevent the clinician from using a medical device among the one or more medical devices until clinician identifying information associated with the mentor clinician is received.

Clause 41. A method comprising: identifying one or more interactions of a first user with one or more medical devices; determining, based on the one or more interactions and a predetermined set of rules, a compliance score associated with the first user; in response to the compliance score not satisfying a threshold compliance score, reducing an access level of the first user to at least one of the one or more medical devices and generating a training program associated with the at least one medical device and the one or more interactions, wherein reducing the access level includes reducing a number of respective features of the at least one medical device that are available to the first user; and automatically, without user involvement, sending a training package associated with the training program to the first user and notifying the first user to complete the training program using the training package.

Clause 42. The method of Clause 41, further comprising: receiving a request for the first user to access the at least one medical device; determining, responsive to the request, that the first user has not completed the training program: requiring authorization from a second user authorized to use the at least one medical device before granting the request for the first user to access the at least one medical device.

Clause 43. The method of Clause 41, wherein the training program is generated based on a category associated with the one or more interactions and includes one or more training tasks associated with the number of respective features of the at least one medical device, and wherein the method further comprises: determining that the first user completed the training program, including the one or more training tasks; and restoring, responsive to determining that the first user completed the training program, the access level of the first user with regard to the at least one medical device.

Clause 44. The method of claim 3, wherein each of the one or more respective features of the medical device are made available to the first user as a corresponding training task associated with each feature is completed by the first user.

Clause 45. A system comprising a memory storing instructions; and one or more processors configured to execute the instructions to cause the system to perform any of the methods of Clauses 41-44.

Clause 46. A non-transitory computer-readable medium storing instructions thereon that, when executed by one or more computing devices, case the one or more computing devices to perform one or more operations comprising any of the method steps of Clauses 41-44.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

While the description discusses certain features using a modular infusion pump as the example medical device, the adaptive control features may be implemented using different medical devices such as stand-alone infusion pumps, syringe pumps, medication preparation workstations, or automated medication dispensing cabinets. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method performed by one or more computing devices, comprising:
   identifying interactions of a first user with a plurality of medical devices in a healthcare organization, one of the interactions including a response time to one or more alarms generated by a respective medical device of the plurality of medical devices, the plurality of medical devices including an infusion device, a syringe pump, a medication preparation workstation, or an automated medication dispensing cabinet;
   determining, based on the identified interactions and a predetermined set of rules, a compliance score associated with the first user;

in response to the compliance score not satisfying a threshold compliance score, automatically, without user involvement:
transmitting an instruction to at least one medical device of the plurality of medical devices to cause an access level of the first user to the at least one medical device to be reduced by denying access to a number of respective features of the at least one medical device that are available to the first user;
generating a training program associated with the at least one medical device;
sending a training package associated with the training program to the first user and notifying the first user to complete the training program using the training package, and
restoring the access level of the first user with regard to the at least one medical device responsive to the first user completing the training program.

2. The method of claim 1, further comprising:
receiving a request for the first user to access the at least one medical device;
determining, responsive to the request, that the first user has not completed the training program;
requiring authorization from a second user authorized to use the at least one medical device before granting the request for the first user to access the at least one medical device.

3. The method of claim 1, wherein the training program is generated based on a category associated with the interactions and includes one or more training tasks associated with the number of respective features of the at least one medical device, and wherein the method further comprises:
determining that the first user completed the training program, including the one or more training tasks.

4. The method of claim 3, wherein each of the one or more respective features of the medical device are made available to the first user as a corresponding training task associated with each feature is completed by the first user.

5. The method of claim 1, further comprising:
assigning a performance score to each of a plurality of users based on medical device interactions performed by the plurality of users with respect to the one or more medical devices;
receiving a first shift schedule associated with the plurality of users;
determining whether the first shift schedule satisfies one or more scheduling criteria associated with a healthcare facility;
in response to determining that the first shift schedule does not satisfy the one or more scheduling criteria and a first performance score for a first user not satisfying a first evaluation threshold of the one or more scheduling criteria: (1) generating a new second shift schedule for the plurality of users that replaces a first user scheduled during a first time period with a second user not currently scheduled during the time period based on a second performance score of the second user, and (2) electronically preventing the first user from using at least one of the one or more medical devices during the first time period; and
causing the new schedule for the shift to be displayed on a display device associated with a user scheduling system.

6. The method of claim 5, further comprising:
identifying, based on performance scores of a subset of the plurality of users, one or more high performing resource centers;
generating a request for one or more users not among the plurality of users from the one or more high performing resource centers; and
transmitting the request to the user scheduling system.

7. The method of claim 5, further comprising:
determining a subset of the plurality of users whose performance scores satisfy a threshold low performance score;
receiving information related to interactions of a user of the subset with a medical device;
identifying, based on the information, a workflow initiated at the medical device;
identifying, based on the workflow and a set of stored rules, a next step in the workflow; and
causing the next step to be displayed on a display device associated with medical device.

8. The method of claim 7, further comprising:
determining, based on the information related to the interactions, one or more follow-up activities for the user; and
generating an alert for the one or more follow-up activities;
transmitting the alert for the one or more follow-up activities to a computing device associated with the user;
determining, based on the one or more follow-up activities, whether an update to an electronic record of a patient at an administration system of the healthcare facility is required; and
in response to determining that an update to the electronic record is required, causing the alert to be displayed adjacent to the electronic record on a display device associated with to the administration system.

9. The method of claim 5, further comprising:
receiving information related to a set of interactions of a user of the plurality of users with a medical device;
identifying a predetermined care area of the medical device based on location information of the medical device;
determining, based on the information, a parameter value associated with a medication administered to a patient;
in response to determining that the parameter value is outside of a predetermined threshold value, updating a medication counter associated with the predetermined care area, wherein the medication counter indicates a number of times the medication is administered using a parameter value outside of the predetermined threshold value;
determining whether the medication counter satisfies a second threshold value; and
in response to determining that the medication counter satisfies the second threshold value, causing an alert identifying the medication and the predetermined care area to be displayed on a display device of a drug management system.

10. The method of claim 9, further comprising:
in response to determining that the counter satisfies the threshold value, calculating, based at least on the value for the parameter of the medication at which the medication is administered, a new value for the parameter; and
transmitting an alert to a user of the drug management system to update a current value of the parameter to the new value for the parameter.

11. The method of claim 9, further comprising:
in response to determining that the medication counter does not satisfy the second threshold value, reducing the performance score of the user by a predetermined amount;
determining whether the reduced performance score satisfies a predetermined threshold low performance score; and
in response to determining that the reduced performance score satisfies the predetermined threshold low performance score, updating permissions of associated with the user to electronically prevent the user from using the one or more medical devices.

12. The method of claim 9, further comprising:
in response to determining that the reduced performance score satisfies a predetermined threshold low performance score, assigning a mentor user to the user; and
electronically preventing the user from using a medical device among the one or more medical devices until user identifying information associated with the mentor user is received.

13. A system comprising:
a memory storing instructions; and
one or more processors configured to execute the instructions to cause the system to:
identify interactions of a first user with a plurality of medical devices in a healthcare organization, one of the interactions including a response time to one or more alarms generated by a respective medical device of a plurality of medical devices, the plurality of medical devices including an infusion device, a syringe pump, a medication preparation workstation, or an automated medication dispensing cabinet;
determine, based on the identified interactions and a predetermined set of rules, a compliance score associated with the first user;
in response to the compliance score not satisfying a threshold compliance score, automatically, without user involvement:
transmit an instruction to at least one medical device of the plurality of medical devices to cause an access level of the first user to the at least one medical device to be reduced by denying access to a number of respective features of the at least one medical device that are available to the first user; and
generate a training program associated with the at least one medical device;
send a training package associated with the training program to the first user and notifying the first user to complete the training program using the training package; and
restore the access level of the first user with regard to the at least one medical device responsive to the first user completing the training program.

14. The system of claim 13, wherein the one or more processors are configured to execute the instructions to further cause the system to:
receive a request for the first user to access the at least one medical device;
determine, responsive to the request, that the first user has not completed the training program;
require authorization from a second user authorized to use the at least one medical device before granting the request for the first user to access the at least one medical device.

15. The system of claim 13, wherein the one or more processors are configured to execute the instructions to further cause the system to:
determine that the first user completed the training program.

16. The system of claim 15, wherein the training program is generated based on a category associated with the one or more interactions and includes one or more training tasks associated with the number of respective features of the at least one medical device, and wherein each of the one or more respective features of the medical device are made available to the first user as a corresponding training task associated with each feature is completed by the first user.

17. The system of claim 13, wherein the one or more processors are configured to execute the instructions to further cause the system to:
assign a performance score to each of a plurality of users based on medical device interactions performed by the plurality of users with respect to the one or more medical devices;
receive a first shift schedule associated with the plurality of users;
determine whether the first shift schedule satisfies one or more scheduling criteria associated with a healthcare facility;
in response to determining that the first shift schedule does not satisfy the one or more scheduling criteria and a first performance score for a first user not satisfying a first evaluation threshold of the one or more scheduling criteria: (1) generate a new second shift schedule for the plurality of users that replaces a first user scheduled during a first time period with a second user not currently scheduled during the time period based on a second performance score of the second user, and (2) electronically prevent the first user from using at least one of the one or more medical devices during the first time period; and
cause the new schedule for the shift to be displayed on a display device associated with a user scheduling system.

18. The system of claim 17, wherein the one or more processors are configured to execute the instructions to further cause the system to:
determine a subset of the plurality of users whose performance scores satisfy a threshold low performance score;
receive information related to interactions of a user of the subset with a medical device;
identify, based on the information, a workflow initiated at the medical device;
identify, based on the workflow and a set of stored rules, a next step in the workflow; and
cause the next step to be displayed on a display device associated with medical device.

19. The system of claim 18, wherein the one or more processors are configured to execute the instructions to further cause the system to:
determine, based on the information related to the one or more interactions, one or more follow-up activities for the user; and
generate an alert for the one or more follow-up activities;
transmit the alert for the one or more follow-up activities to a computing device associated with the user;
determine, based on the one or more follow-up activities, whether an update to an electronic record of a patient at an administration system of the healthcare facility is required; and in response to determining that an update to the electronic record is required, cause the alert to be displayed adjacent to the electronic record on a display device associated with to the administration system.

20. The system of claim 13, wherein the one or more processors are configured to execute the instructions to further cause the system to:
   identify a predetermined care area of the medical device based on location information of the medical device;
   determine, based on the information, a parameter value associated with a medication administered to a patient;
   in response to determining that the parameter value is outside of a predetermined threshold value, update a medication counter associated with the predetermined care area, wherein the medication counter indicates a number of times the medication is administered using a parameter value outside of the predetermined threshold value;
   determine whether the medication counter satisfies a second threshold value; and
   in response to determining that the medication counter satisfies the second threshold value, cause an alert identifying the medication and the predetermined care area to be displayed on a display device of a drug management system.

21. The system of claim 20, wherein the one or more processors are configured to execute the instructions to further cause the system to:
   in response to determining that the medication counter does not satisfy the second threshold value, reduce the performance score of the user by a predetermined amount;
   assign a mentor user to the user responsive to determining that the reduced performance score satisfies a predetermined threshold low performance score; and
   electronically prevent the user from using a medical device among the one or more medical devices until user identifying information associated with the mentor user is received.

22. A non-transitory computer-readable medium storing instructions thereon that, when executed by one or more computing devices, case the one or more computing devices to perform one or more operations comprising:
   identify interactions of a first user with a plurality of medical devices in a healthcare organization, one of the interactions including a response time to one or more alarms generated by a respective medical device of a plurality of medical devices, the plurality of medical devices including an infusion device, a syringe pump, a medication preparation workstation, or an automated medication dispensing cabinet;
   determine, based on the identified interactions and a predetermined set of rules, a compliance score associated with the first user;
   in response to the compliance score not satisfying a threshold compliance score, automatically, without user involvement:
      transmit an instruction to at least one medical device of the plurality of medical devices to cause an access level of the first user to the at least one medical device to be reduced by denying access to a number of respective features of the at least one medical device that are available to the first user; and
      generate a training program associated with the at least one medical device;
      send a training package associated with the training program to the first user and notifying the first user to complete the training program using the training package; and
   restore the access level of the first user with regard to the at least one medical device responsive to the first user completing the training program.

* * * * *